US012606557B2

(12) United States Patent
Huryn et al.

(10) Patent No.: US 12,606,557 B2
(45) Date of Patent: Apr. 21, 2026

(54) SUBSTITUTED INDOLES WITH INHIBITORY ACTIVITY

(71) Applicant: UNIVERSITY OF PITTSBURGH—OF THE COMMONWEALTH SYSTEM OF HIGHER EDUCATION, Pittsburgh, PA (US)

(72) Inventors: Donna Huryn, Allentown, NJ (US); Neil Hukriede, Allison Park, PA (US); Keith Long, Pittsburgh, PA (US); Jagannath Panda, Pittsburgh, PA (US); Sipak Joyasawal, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 656 days.

(21) Appl. No.: 17/927,406

(22) PCT Filed: May 27, 2021

(86) PCT No.: PCT/US2021/034513
§ 371 (c)(1),
(2) Date: Nov. 23, 2022

(87) PCT Pub. No.: WO2021/243018
PCT Pub. Date: Dec. 2, 2021

(65) Prior Publication Data

US 2023/0192684 A1 Jun. 22, 2023

Related U.S. Application Data

(60) Provisional application No. 63/030,675, filed on May 27, 2020.

(51) Int. Cl.

| | |
|---|---|
| ***C07D 471/04*** | (2006.01) |
| ***C07D 209/08*** | (2006.01) |
| ***C07D 413/04*** | (2006.01) |

(52) U.S. Cl.
CPC ......... *C07D 471/04* (2013.01); *C07D 209/08* (2013.01); *C07D 413/04* (2013.01)

(58) Field of Classification Search
CPC .................................................... C07D 471/04
USPC .......................................................... 514/300
See application file for complete search history.

(56) References Cited

U.S. PATENT DOCUMENTS

| | | | | |
|---|---|---|---|---|
| 5,410,061 A * | 4/1995 | Gilmore | A61P 13/02 | 546/152 |
| 6,069,156 A * | 5/2000 | Oku | A61P 27/14 | 548/465 |
| 6,218,388 B1 | 4/2001 | Boschelli et al. | | |
| 6,358,992 B1 * | 3/2002 | Pamukcu | A61K 31/404 | 514/415 |
| 6,410,584 B1 * | 6/2002 | Pamukcu | A61K 31/4985 | 514/416 |

FOREIGN PATENT DOCUMENTS

| | | | |
|---|---|---|---|
| JP | 64-67682 | * 3/1989 | |
| JP | 10114654 | * 10/1996 | |
| WO | 9815530 | * 4/1998 | |
| WO | WO-9815530 A1 | * 4/1998 | C07D 405/12 |

OTHER PUBLICATIONS

International Search Report and Written Opinion in PCT/US2021/034513. Mailed Oct. 13, 2021. 10 pages.
Whitehouse et al. "Development of inhibitors against *Mycobacterium abscessus* tRNA Methyltransferase (TrmD) using fragment-based approaches" J. Med. Chem. 2019.
PubChem-SID-24880873, Modify Date: Mar. 14, 2018.

* cited by examiner

*Primary Examiner* — Niloofar Rahmani
(74) *Attorney, Agent, or Firm* — Meunier Carlin & Curfman LLC

(57) ABSTRACT

Disclosed are substituted indole compounds and compositions. The substituted indole compounds and compositions can be used for treating or preventing acute renal failure in a subject. The compounds and compositions can also be used for treating an infectious disease or cancer.

17 Claims, 4 Drawing Sheets

| | HDAC8 HaloTag DMSO | HDAC8 HaloTag UPHH 171 |
|---|---|---|
| V50 | 51.83 | 58.96 |

SUBSTITUTED INDOLES WITH INHIBITORY ACTIVITY

CROSS REFERENCE TO RELATED APPLICATIONS

This application is a U.S. National Stage application filed under 35 U.S.C. § 371 of PCT/US2021/034513 filed May 27, 2021, which claims the benefit of priority to U.S. Provisional Application No. 63/030,675, filed May 27, 2020, which is incorporated by reference herein in its entirety

STATEMENT REGARDING FEDERALLY SPONSORED RESEARCH

This invention was made with government support under grant W81XWH-17-1-0610 awarded by the U.S. Army Medical Research and Materiel Command. The government has certain rights in the invention.

BACKGROUND

Episodes of Acute Kidney Injury (AKI) result in a long-term reduction in renal functional reserve such that affected patients are at an increased risk of developing progressive chronic kidney disease (CKD) leading to end-stage renal disease (ESRD) requiring life-long dialysis. At present, no therapies have been proven to reduce AKI driven, post-injury CKD progression. Since AKI is an acute, but commonly reoccurring event in patients with CKD, short-term therapies that prevent the onset or progression of CKD by enhancing post-AKI repair are particularly attractive to prevent this chronic debilitating disease. Failure to develop effective therapies for AKI has occurred, in part, because patients often present late in the course of AKI, so that effective therapies need to reverse established injury, or rapidly promote repair. Many of the experimental drugs that have been found to be ineffective in clinical trials for AKI, were only effective in experimental models of AKI when given before the initiating injury. In addition, failure to model the nature of the injury on backgrounds of aging, diabetes and CKD that are common in patients with AKI, may account for the failure of pre-clinical leads to translate into clinical practice. There is an need for efficacious drugs for enhancing recovery after an initiating injury, and which improve kidney function in people with associated conditions, notably diabetes and old age, that affect active combat and retired military personnel. The compounds, compositions, and methods disclosed herein address these and other needs.

There is also a need for compounds, compositions, and methods for preventing and treating cancer and infectious diseases. In this regard, the compounds disclosed herein are believed to be histone deacetylase (HDAC) inhibitors as well as inhibitors of other metallo enzymes. HDACs have been linked to cancer, as well as other health conditions.

SUMMARY

In accordance with the purposes of the disclosed materials and methods, as embodied and broadly described herein, the disclosed subject matter, in one aspect, relates to compounds, compositions and methods of making and using compounds and compositions. The compounds and compositions can be used for treating or preventing renal injury in a subject. In some aspects, the methods are directed to protecting a kidney from acute renal injury or from chronic renal injury. The renal injury may be associated with the pre-existence in the subject of one or more known risk factors for prerenal, intrinsic renal, or postrenal acute renal failure.

The compounds are also suitable for use in treating cancer. The compounds can be used alone or in combination with other anticancer treatments, such as surgery and/or radiation. Methods of treating cancer can include administering to the subject a composition comprising a compound disclosed herein. The cancer can be selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

The compounds are further suitable for use in treating an infectious disease. The methods for treating an infectious disease can include administering to the subject, a therapeutic effective amount of a compound disclosed herein. The infectious disease can be associated with a microbial infection, such as a bacterial infection, a parasitic infection, a viral infection, or a fungal infection.

The compounds for use and disclosed herein are substituted indole compounds having a structure according to Formula I:

Formula I

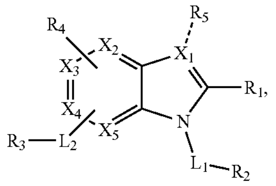

wherein $X_1$ is selected from $CR_5$ or N, $X_2$, $X_3$, $X_4$, and $X_5$ are independently selected from CH, $CL_2R_3$, $CR_4$, or N, $L_1$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_1$ is optionally substituted with one or more groups;

$L_2$ is a linker selected from bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_2$ is optionally substituted with one or more groups;

$R_1$ is selected from hydrogen, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_1$-$C_6$ alkylamine, $C_1$-$C_6$ heteroalkyl, cycloalkyl, heterocycloalkyl, aryl, heteroaryl, wherein $R_1$ is optionally substituted or unsubstituted;

$R_2$ is selected from hydrogen, cycloalkyl, cycloalkenyl, heterocycloalkyl, heteroalkyl, cycloheteroalkenyl, aryl, heteroaryl, wherein $R_2$ is optionally substituted with one or more groups selected from halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, ether, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", —$SF_5$, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R", and R'" can combine and form a ring;

$R_3$ is selected from a metal (for e.g., Zn) chelating group, an acid group, or an acid isostere;

$R_4$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, hydroxamic acid, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", $SF_5$, cycloalkyl, cycloalkenyl, heterocycloalkyl, heteroalkyl, cycloheteroalkenyl, aryl, heteroaryl, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R", and R'" can combine and form a ring, and wherein $R_4$ is optionally substituted with one or more groups;

$R_5$ when present, is selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkoxy, $C_1$-$C_6$ heteroalkyl, substituted or unsubstituted aryl, $C_1$-$C_6$ alkylamine, or —$Y_2$—$R_6$; $Y_2$ is $C_1$-$C_6$ alkylene, $C_1$-$C_6$ haloalkylene, $C_2$-$C_6$ alkenylene, or $C_2$-$C_6$ heteroalkylene; $R_6$ is selected from hydrogen, halogen, cyano, hydroxy, amino, $C_1$-$C_6$ alkylamino, $C_1$-$C_6$ alkoxy, $C_3$-$C_8$ cycloalkyl, substituted or unsubstituted $C_2$-$C_8$ heterocycloalkyl, substituted or unsubstituted aryl, substituted or unsubstituted heteroaryl, or —$Y_3$—$R_7$; $Y_3$ is a bond, —O—, —S—, —SO—, —$SO_2$—, —NR'—, —CO—, —C(O)O—, —OC(O)—, NHC(O)—, —C(O)NR'—, —$SO_2$NR'—, —NH$SO_2$—, —OC(O)NR'—, —NHC(O)O—, —OC(O)O—, —NHC(O)NR'—; wherein R' is selected from hydrogen and $C_1$-$C_4$ alkyl; $R_7$ is hydrogen, $C_1$-$C_6$ alkyl, $C_2$-$C_6$ alkenyl, $C_1$-$C_6$ heteroalkyl, $C_1$-$C_6$ haloalkyl, substituted or unsubstituted $C_3$-$C_8$ cycloalkyl, substituted or unsubstituted heterocycloalkyl, substituted or unsubstituted aryl, or substituted or unsubstituted heteroaryl,

- - - - is a bond that can be present or absent;

or a pharmaceutically acceptable salt, ester, or prodrug thereof.

As disclosed herein, the compounds contemplates each possible isomer (including stereoisomers), e.g., each enantiomer, diastereomer, and meso compound, and a mixture of isomers, such as a racemic or scalemic mixture.

In some aspects, $R_3$ is —CONH—OR", wherein R" is selected from hydrogen or $C_1$-$C_3$ alkyl. In other aspects, $R_3$ is not —CONH—OH.

In the methods disclosed herein, the compounds can be administered with an additional therapeutically active co-agent used in the treatment of the condition.

DETAILED DESCRIPTION

Figure 1:
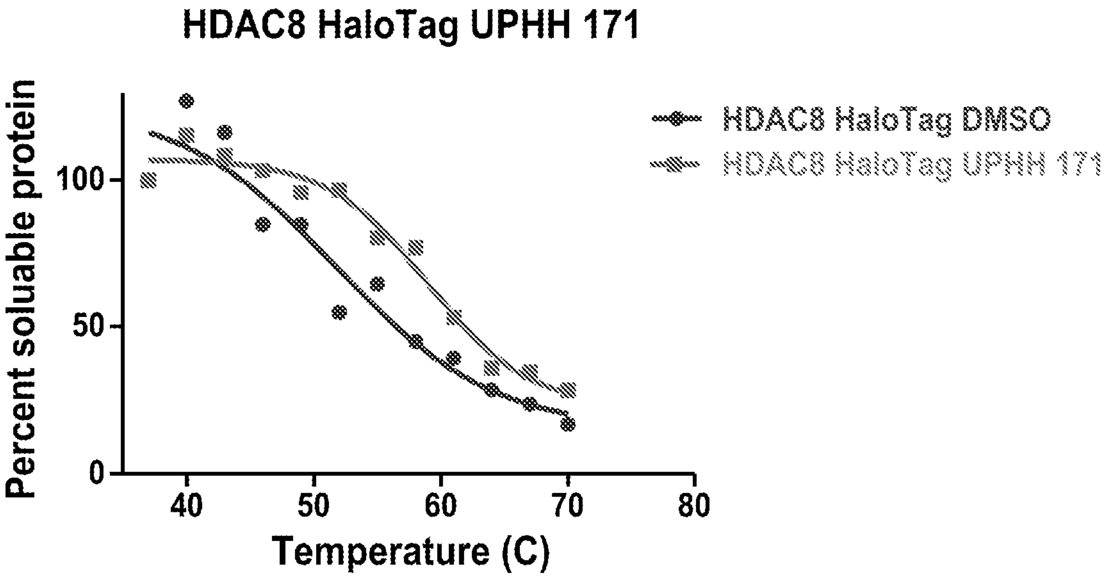
FIG. 1 is a graph showing increased thermal stability of UPHH171 bound to $HDAC_8$ in CETSA assay.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an analog" includes mixtures of two or more such analogs, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. In some examples, the substituent can include one or more groups selected from, but not limited to, alkyl, alkoxy, alkenyl, alkynyl, aryl, heteroaryl, aldehyde, acetamide, amino, amide, cycloalkyl, cycloalkenyl, carbonyl, carboxylic acid, cyano, ester, ether, halide, halogenated alkyl, heteroalkyl, heterocycloalkyl, hydroxy, ketone, nitro, oxo, dioxo, silyl, sulfo-oxo, sulfonyl, sulfonamide, sulfone, sulfoxide, thiol, or a combination thereof, as described herein.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols R", X", or L" is used herein as merely a generic substituent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond.

Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. The cycloalkyl group can include 3 or more carbon atoms, such as 3, 4, 5, 6, 7, 8, 9, or 10 carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. The cycloalkyl group can include 3 or more carbon atoms, such as 3, 4, 5, 6, 7, 8, 9, or 10 carbon atoms. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H.

Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O—.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

The compounds disclosed herein can be prepared and/or administered as single enantiomers (enantiomerically pure and having an enantiomeric excess of >90%, preferably at least 97%, more preferably at least 99%), enantiomerically enriched (one of the enantiomers of a compound is present in excess compared to the other enantiomer), diastereomerically pure (having a diastereomeric p excess of >90%, preferably at least 97%, more preferably at least 99%), diastereomerically enriched (one of the diastereomers of a compound is present in excess compared to the other diastereomer), or as a racemic mixture (an equimolar mixture of two enantiomeric components).

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Pharmaceutical compositions disclosed herein may be in the form of pharmaceutically acceptable salts or prodrugs as generally described below. Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below). When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

The compounds described herein may be administered in the form of prodrugs. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as a prodrug are known, for example, in Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It has been shown that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Disclosed herein are substituted indole compounds having a structure according to Formula I:

Formula I

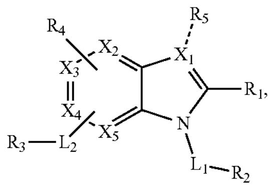

wherein $X_1$ is selected from $CR_5$ or N, $X_2$, $X_3$, $X_4$, and $X_5$ are independently selected from CH, $CL_2R_3$, $CR_4$, or N, $L_1$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_1$ is optionally substituted with one or more groups;

$L_2$ is a linker selected from bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, and wherein $L_2$ is optionally substituted with one or more groups;

$R_1$ is selected from hydrogen, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_1$-$C_6$ alkylamine, $C_1$-$C_6$ heteroalkyl, cycloalkyl, heterocycloalkyl, aryl, heteroaryl, wherein $R_1$ is optionally substituted or unsubstituted;

$R_2$ is selected from hydrogen, cycloalkyl, cycloalkenyl, heterocycloalkyl, heteroalkyl, cycloheteroalkenyl, aryl, heteroaryl, wherein $R_2$ is optionally substituted with one or more groups selected from halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, ether, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", —$SF_5$, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R", and R'" can combine and form a ring;

$R_3$ is selected from a metal (for e.g., Zn) chelating group, an acid group, or an acid isostere, or $R_3$ is selected from hydroxamic acid, heteroalkyl, alkoxy, haloalkoxy, amine, alkylamine, amide, alkylamide, hydroxyl, heteroaryl, heterocycloalkyl, heterocycloalkenyl, aryl, nitro, —CN, —R'COR", —COR", —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —N(OH)COR", —R'N(OH)COR", —CONH(OR"), —R'CONH(OR"), —ONH(COR"), —R'ONH(COR"), —R'CONHCN, —NR'C(═O)—R", —R'$SO_2$NHCOR", —R'CONH$SO_2$R", —SR", —SO—R", —$SO_2$—R", —R'$SO_2$—R", —SO(OR"), —R'SO(OR"), —$SO_2$(OR"), —R'$SO_2$(OR"), —$SO_2$NR'R", —R'$SO_2$NR'R", —NR'$SO_2$R", —CONR'$SO_2$R", —CONR'$SO_2$NR"R'", —NR'$SO_2$(OR"), —C(O)N($CH_2$R')—OR", —O—NR'—COR", —OCONR'R", —NR'CO(OR"), —OCO(OR"), —NHCONH—R", —NHCONHCO—R", —NHCONH$SO_2$—R", —OCO—R", —NR'R", —PO(OR")(R'"), —PO(OR")(OR'"), —R'PO(OR")(OR'"), —C(O)-haloalkyl, substituted cycloalkenyl, dioxocyclopentyl, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, substituted or unsubstituted aryl, alkylaryl, substituted or unsubstituted heteroaryl, alkylheteroaryl or two or more of R', R", and R'" can combine and form a ring, and wherein $R_3$ is optionally substituted with one or more groups;

$R_4$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, hydroxamic acid, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", $SF_5$, cycloalkyl, cycloalkenyl, heterocycloalkyl, heteroalkyl, cycloheteroalkenyl, aryl, heteroaryl, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R", and R'" can combine and form a ring, and wherein $R_4$ is optionally substituted with one or more groups.

$R_5$ when present, is selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkoxy, $C_1$-$C_6$ heteroalkyl, substituted or unsubstituted aryl, $C_1$-$C_6$ alkylamine, or —$Y_2$—$R_6$; $Y_2$ is $C_1$-$C_6$ alkylene, $C_1$-$C_6$ haloalkylene, $C_2$-$C_6$ alkenylene, or $C_2$-$C_6$ heteroalkylene; $R_6$ is selected from hydrogen, halogen, cyano, hydroxy, amino, $C_1$-$C_6$ alkylamino, $C_1$-$C_6$ alkoxy, $C_3$-$C_8$ cycloalkyl, substituted or unsubstituted $C_2$-$C_8$ heterocycloalkyl, substituted or unsubstituted aryl, substituted or unsubstituted heteroaryl, or —$Y_3$—$R_7$; $Y_3$ is a bond, —O—, —S—, —SO—, —$SO_2$—, —NR'—, —CO—, —C(O)O—, —OC(O)—, NHC(O)—, —C(O)NR'—, —$SO_2NR'$—, —$NHSO_2$—, —OC(O)NR'—, —NHC(O)O—, —OC(O)O—, —NHC(O)NR'—; wherein R' is selected from hydrogen and $C_1$-$C_4$ alkyl; $R_7$ is hydrogen, $C_1$-$C_6$ alkyl, $C_2$-$C_6$ alkenyl, $C_1$-$C_6$ heteroalkyl, $C_1$-$C_6$ haloalkyl, substituted or unsubstituted $C_3$-$C_8$ cycloalkyl, substituted or unsubstituted heterocycloalkyl, substituted or unsubstituted aryl, or substituted or unsubstituted heteroaryl, ----- is a bond that can be present or absent;

or a pharmaceutically acceptable salt, ester, or prodrug thereof.

As described herein, $R_3$ can be a metal chelating group, an acid group, or an acid isostere. The term “chelating group” or “chelating agent” as used herein refers to a substance whose molecules can form a bond to a metal. The chelating group can be a monodentate or a multidentate ligand. Examples a chelating agent include organic small molecules, polypeptides, amino acids, and such the like. Chelating groups can be naturally occurring or synthetic. The “metal chelating group” refers to any substance that is able to chelate a metal ion, such as zinc. The metal ion may be within an active site of a biological molecule such as an enzyme. Accordingly, the metal chelating group is capable of inhibiting the activity of metal binding biological molecules such as metalloenzymes. In some examples, the metal chelating group can bind the active site zinc(II) ion of a histone deacetylase. An example for a zinc/metal binding group is the hydroxamic acid group, benzamide, carboxylic acid, thiol, imidazole thione, and such the like. In some embodiments, the zinc binding group is not the hydroxamic acid group. Other representative examples of metal chelating groups are described in Seth M Cohen, *Acc. Chem. Res.*, 2017, 50, 8: 2007-2016, the contents of which are incorporated herein by reference.

The “acid group” as used herein refers to an acidic functional group such as —$CO_2H$, —O—$SO_3H$, —$PO_3H$, —O—$PO_3H$, and the like.

The term “acid isostere” as used herein refers to a functional group or a moiety that elicits similar physical, biological and/or chemical properties as that of an acid moiety, such as a carboxylic acid moiety. For example, the acid isostere can ionize to bear a net negative charge, or act as a proton donor or acceptor. Representative examples of acid isosteres are described in Pierrik Lassalas et al., *J. Med. Chem.* 2016, 59, 7: 3183-3203; U.S. Pat. Nos. 10,105,373 and 7,208,601, the contents of which are incorporated herein by reference. In some embodiments, the acid isostere can include hydroxamic acid, hydroxamic esters, phosphonic acid, phosphinic acid, sulfonic acid, sulfinic acid, sulfonamides, acyl sulfonamides, sulfonylurea, acylurea, heteroaryl groups (such as tetrazole and isoxazole), thiazolidine dione, oxazolidine dione, oxadiazol-5(4H)-one, thiadiazol-5(4H)-one, oxathiadiazole-2-oxide, oxadiazol-5(4H)-thione, tetramic acid, cyclopentane-1,3-diones, cyclopentane 1,2-diones, squaric acid derivatives, and substituted phenols. For example, the acid isosteres include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, 5-hydroxy-4H-pyran-4-on-2-yl, 1,2,5-thiadiazolidin-3-one-1,1-dioxide-4-yl, 1,2-5-thiadiazolidin-3-one-1,1-dioxide-5-yl, 1,2,5-thiadiazolidin-3-one-1,1-dioxide-5-yl having substituents at the 2 and/or 4 position; or —N-acyl-alkylsulfonamide.

In some aspects of Formula I, the indole compound can have a structure according to Formula I-A:

Formula I-A

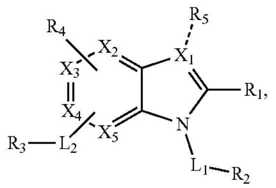

wherein $X_1$ is selected from $CR_5$ or N, $X_2$, $X_3$, $X_4$, and $X_5$ are independently selected from CH, $CL_2R_3$, $CR_4$, or N, (wherein C defines a carbon atom and N defines a nitrogen atom throughout the present disclosure);

$L_1$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_1$ is optionally substituted with one or more groups;

$L_2$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_2$ is optionally substituted with one or more groups;

$R_1$ is selected from hydrogen, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_1$-$C_6$ alkylamine, $C_1$-$C_6$ heteroalkyl, cycloalkyl, heterocycloalkyl, aryl, or heteroaryl, wherein $R_1$ is optionally substituted or unsubstituted;

$R_2$ is selected from hydrogen, cycloalkyl, cycloalkenyl, heterocycloalkyl, heteroalkyl, cycloheteroalkenyl, aryl, or heteroaryl, wherein $R_2$ is optionally substituted with one or more groups selected from halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, ether, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(=O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", or —NR'R", —$SF_5$, wherein R', R", and R'" are independently absent or selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkyl aryl, heteroaryl, or alkyl heteroaryl or two or more of R', R", and R'" can combine and form a ring;

$R_3$ is selected from a metal (for e.g., Zn) chelating group, an acid group, or acid isostere, such as —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —N(OH)COR", —R'N(OH)COR", —CONH(OR"), —R'CONH(OR"), —ONH(COR"), —R'ONH(COR"), —R'CONHCN, —NR'C(=O)—R", —R'$SO_2$NHCOR", —R'CONH$SO_2$R", —SR", —SOR", —$SO_2$—R", —R'$SO_2$—R", —SO(OR"), —R'SO(OR"), —$SO_2$(OR"), —R'$SO_2$(OR"), —$SO_2$NR'R", —R'$SO_2$NR'R", —NR'$SO_2$R", —CONR'$SO_2$R", —CONR'$SO_2$NR"R'", —NR'$SO_2$(OR"), —C(O)N($CH_2$R')—OR", —O—NR'—COR", —OCONR'R", —NR'CO(OR"), —OCO(OR"), —NHCONH—R", —NHCONHCO—R", —NHCONH$SO_2$—R", —OCO—R", —NR'R", —$PO_2$H—R", —$PO_3$R", —R'$PO_3$R", —PO(OR")(R'"), —PO(OR")(OR'"), —R'PO(OR")(OR'"), —C(O)— haloalkyl, substituted cycloalkenyl, substituted or unsubstituted dioxocyclopentyl, heterocycloalkyl, heteroalkyl, heterocycloalkenyl, aryl, or heteroaryl, wherein R', R", and R'" are independently absent or selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, substituted or unsubstituted aryl, alkyl aryl, substituted or unsubstituted heteroaryl, or alkyl heteroaryl or two or more of R', R", and R'" can combine and form a ring, and wherein $R_3$ is optionally substituted with one or more groups;

$R_4$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(=O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", cycloalkyl, cycloalkenyl, heterocycloalkyl, heteroalkyl, cycloheteroalkenyl, aryl, or heteroaryl, $SF_5$, wherein R', R", and R'" are independently absent or selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R", and R'" can combine and form a ring, and wherein $R_4$ is optionally substituted with one or more groups;

$R_5$ when present, is selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkoxy, $C_1$-$C_6$ heteroalkyl, $C_1$-$C_6$ alkylamine, substituted or unsubstituted aryl, substituted or unsubstituted heteroaryl, or —$Y_2$—$R_6$; wherein $Y_2$ is selected from $C_1$-$C_6$ alkylene, $C_1$-$C_6$ haloalkylene, $C_2$-$C_6$ alkenylene, or $C_2$-$C_6$ heteroalkylene; $R_6$ is selected from hydrogen, halogen, cyano, hydroxy, amino, $C_1$-$C_6$ alkylamino, $C_1$-$C_6$ alkoxy, $C_3$-$C_8$ cycloalkyl, substituted or unsubstituted $C_2$-$C_8$ heterocycloalkyl, substituted or unsubstituted aryl, substituted or unsubstituted heteroaryl, or —$Y_3$—$R_7$; $Y_3$ is a bond, —O—, —S—, —SO—, —$SO_2$—, —NR'—, —CO—, —C(O)O—, —OC(O)—, NHC(O)—, —C(O)NR'—, —$SO_2$NR'—, —NH$SO_2$—, —OC(O)NR'—, —NHC(O)O—, —OC(O)O—, —NHC(O)NR'—; wherein R' is selected from hydrogen and $C_1$-$C_4$ alkyl; and $R_7$ is selected from hydrogen, $C_1$-$C_6$ alkyl, $C_2$-$C_6$ alkenyl, $C_1$-$C_6$ heteroalkyl, $C_1$-$C_6$ haloalkyl, substituted or unsubstituted $C_3$-$C_8$ cycloalkyl, substituted or unsubstituted heterocycloalkyl, substituted or unsubstituted aryl, or substituted or unsubstituted heteroaryl, ----- is a bond that can be present or absent;

or a pharmaceutically acceptable salt, ester, or prodrug thereof.

In some embodiments of Formulas I and I-A, the indole compound can have a structure according to Formula I-A-1:

Formula I-A-1

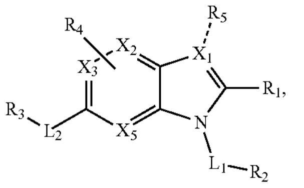

or a pharmaceutically acceptable salt, wherein $X_1$, $X_2$, $X_3$, $X_5$, $L_1$, $L_2$, $R_1$, $R_2$, $R_3$, $R_4$, and $R_5$ are as defined herein with respect to Formula I or Formula I-A.

In some embodiments of Formulas I, the indole compound can have a structure according to Formula I-B:

Formula I-B

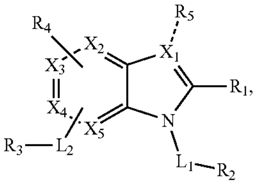

wherein $X_1$ is selected from $CR_5$ or N, $X_2$, $X_3$, $X_4$, and $X_5$ are independently selected from CH, $CL_2R_3$, $CR_4$, or N, wherein at least one of $X_2$, $X_3$, $X_4$, and $X_5$ is N, $L_1$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_1$ is optionally substituted with one or more groups;

$L_2$ is a linker selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R'" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring, and wherein $L_2$ is optionally substituted with one or more groups;

$R_1$ is selected from hydrogen, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_1$-$C_6$ alkylamine, $C_1$-$C_6$ heteroalkyl, cycloalkyl, heterocycloalkyl, aryl, or heteroaryl, wherein $R_1$ is optionally substituted or unsubstituted;

$R_2$ is selected from hydrogen, cycloalkyl, cycloalkenyl, heterocycloalkyl, heteroalkyl, cycloheteroalkenyl, aryl, or heteroaryl, wherein $R_2$ is optionally substituted with one or more groups selected from halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, ether, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", or —NR'R", —$SF_5$, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkyl aryl, heteroaryl, or alkyl heteroaryl or two or more of R', R", and R'" can combine and form a ring;

$R_3$ is selected from a metal (for e.g., Zn) chelating group, an acid group, or an acid isostere, such as —R'$CO_2$H, —$CO_2$R", —R'$CO_2$R", —$CONH_2$, —R'$CONH_2$, —CONHR", —R'CONHR", —CONR"R'", —R'CONR"R'", —R'CONHOH, —N(OH)COR", —R'N(OH)COR", —CONH(OR"), —R'CONH(OR"), —ONH(COR"), —R'ONH(COR"), —R'CONHCN, —NR'C(═O)—R", —R'$SO_2$NHCOR", —R'CONH$SO_2$R", —$SO_2$—R", —R'$SO_2$—R", —SO(OR"), —R'SO(OR"), —$SO_2$(OR"), —R'$SO_2$(OR"), —$SO_2$NR'R", —R'$SO_2$NR'R", —NR'$SO_2$R", —CONR'$SO_2$R", —CONR'$SO_2$NR"R'", —NR'$SO_2$(OR"), —C(O)N($CH_2$R')—OR", —O—NR'—COR", —OCONR'R", —NR'CO(OR"), —OCO(OR"), —NHCONH—R", —NHCONHCO—R", —NHCONH$SO_2$—R", —OCO—R", —NR'R", —PO(OR")(R'"), —PO(OR")(OR'"), —R'PO(OR")(OR'"), cycloalkenyl, heterocycloalkyl, heteroalkyl, heterocycloalkenyl, aryl, or heteroaryl, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, substituted or unsubstituted aryl, alkyl aryl, substituted or unsubstituted heteroaryl, or alkyl heteroaryl or two or more of R', R", and R'" can combine and form a ring, and wherein $R_3$ is optionally substituted with one or more groups;

$R_4$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, —R'$CO_2$H, —$CO_2$R", —R'$CO_2$R", —$CONH_2$, —R'$CONH_2$, —CONHR", —R'CONHR", —CONR"R'", —R'CONR"R'", —CONHOH, —R'CONHOH, —R'CONHCN, —NR'C(═O)—R", —SR", —SO—R", —$SO_2$—R", —R'$SO_3$R", —R'$SO_2$NHCOR", —R'CONH$SO_2$R", —$SO_2$NR'R", —R'$SO_2$NR'R", —NR'$SO_2$R", —OCONR'R", —NR'$CO_2$—R", —$OCO_2$—R", —NHCONH—R", —OCO—R", —NR'R", cycloalkyl, cycloalkenyl, heterocycloalkyl, heteroalkyl, cycloheteroalkenyl, aryl, or heteroaryl, $SF_5$, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl, alkylheteroaryl or two or more of R', R'', and R''' can combine and form a ring, and wherein $R_4$ is optionally substituted with one or more groups;

$R_5$ when present, is selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkoxy, $C_1$-$C_6$ heteroalkyl, $C_1$-$C_6$ alkylamine, substituted or unsubstituted aryl, substituted or unsubstituted heteroaryl, or —$Y_2$—$R_6$; wherein $Y_2$ is selected from $C_1$-$C_6$ alkylene, $C_1$-$C_6$ haloalkylene, $C_2$-$C_6$ alkenylene, or $C_2$-$C_6$ heteroalkylene; $R_6$ is selected from hydrogen, halogen, cyano, hydroxy, amino, $C_1$-$C_6$ alkylamino, $C_1$-$C_6$ alkoxy, $C_3$-$C_8$ cycloalkyl, substituted or unsubstituted $C_2$-$C_8$ heterocycloalkyl, substituted or unsubstituted aryl, substituted or unsubstituted heteroaryl, or —$Y_3$—$R_7$; $Y_3$ is a bond, —O—, —S—, —SO—, —$SO_2$—, —NR'—, —CO—, —C(O)O—, —OC(O)—, NHC(O)—, —C(O)NR'—, —$SO_2$NR'—, —$NHSO_2$—, —OC(O)NR'—, —NHC(O)O—, —OC(O)O—, —NHC(O)NR'—; wherein R' is selected from hydrogen and $C_1$-$C_4$ alkyl; and $R_7$ is selected from hydrogen, $C_1$-$C_6$ alkyl, $C_2$-$C_6$ alkenyl, $C_1$-$C_6$ heteroalkyl, $C_1$-$C_6$ haloalkyl, substituted or unsubstituted $C_3$-$C_8$ cycloalkyl, substituted or unsubstituted heterocycloalkyl, substituted or unsubstituted aryl, or substituted or unsubstituted heteroaryl, ----- is a bond that can be present or absent;

or a pharmaceutically acceptable salt, ester, or prodrug thereof.

In some embodiments of Formulas I and I-B, the compound can have a structure according to Formula I-B-1:

Formula I-B-1

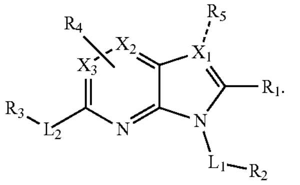

or a pharmaceutically acceptable salt, wherein $X_1$, $X_2$, $X_3$, $L_1$, $L_2$, $R_1$, $R_2$, $R_3$, $R_4$, and $R_5$ are as defined herein with respect to Formula I or Formula I-B.

In some embodiments of Formula I, I-A, I-A-1, I-B, or I-B-1, the indole compound can have a structure according to Formula I-A-2 or Formula I-A-2':

Formula I-A-2

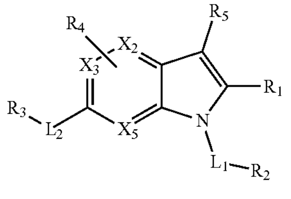

Formula I-A-2'

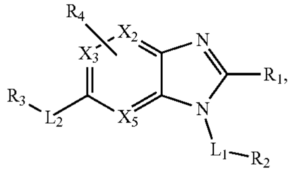

or a pharmaceutically acceptable salt, wherein $X_2$, $X_3$, $X_5$, $L_1$, $L_2$, $R_1$, $R_2$, $R_3$, $R_4$, and $R_5$ are as defined herein with respect to Formula I, Formula I-A, or Formula I-B.

In some embodiments of Formulas I, I-A, I-A-1, I-B, or I-B-1, the indole compound can have a structure according to Formula I-A-3, I-A-3', I-A-4, I-A-4', I-A-5, I-A-5', I-A-6, I-A-6', I-A-7, I-A-7', I-A-8, I-A-8', I-A-9, or I-A-9':

Formula I-A-3

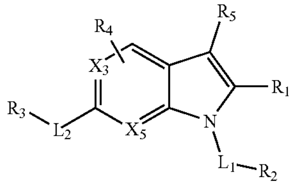

Formula I-A-3'

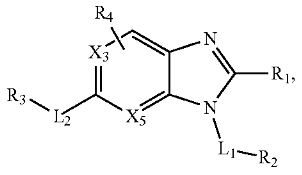

Formula I-A-4

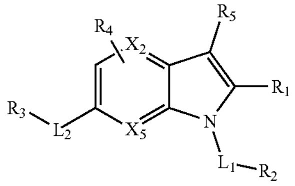

Formula I-A-4'

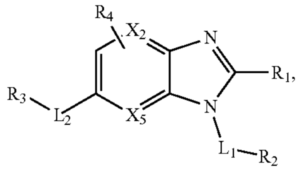

Formula I-A-5

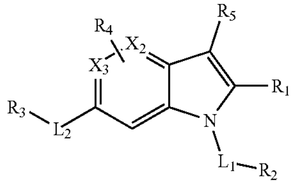

Formula I-A-5'

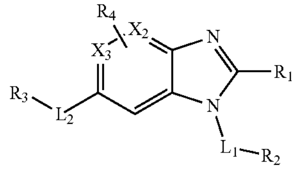

Formula I-A-6

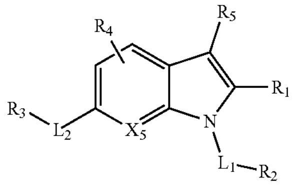

-continued

Formula I-A-6'

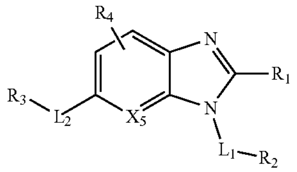

Formula I-A-7

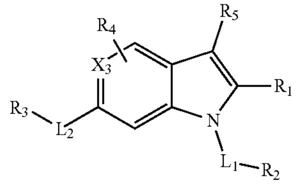

Formula I-A-7'

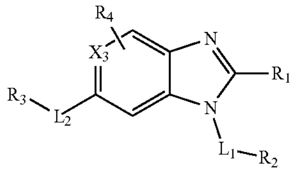

Formula I-A-8

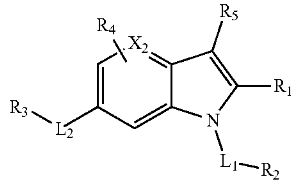

Formula I-A-8'

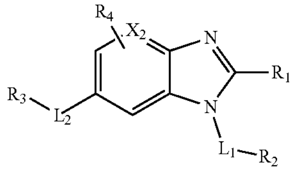

Formula I-A-9

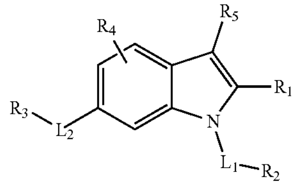

Formula I-A-9'

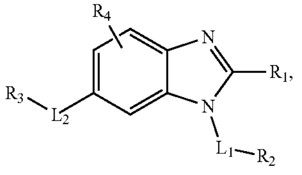

or a pharmaceutically acceptable salt, wherein $X_2$, $X_3$, $X_5$, $L_1$, $L_2$, $R_1$, $R_2$, $R_3$, $R_4$, and $R_5$ are as defined herein with respect to Formula I, Formula I-A or Formula I-B.

In some embodiments of the formulas described herein (Formula I, I-A, I-B, I-B-1, I-A-1 to I-A-9, or I-A-1' to I-A-9'), $X_1$ can be $CR_5$, wherein $R_5$ is as defined herein. For example, $R_5$ can be selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkoxy, $C_1$-$C_6$ heteroalkyl, $C_1$-$C_6$ alkylamine, substituted or unsubstituted aryl, substituted or unsubstituted heteroaryl, or —$Y_2$—$R_6$. In some embodiments, $X_1$ can be N. In some embodiments, $X_1$ can be CH.

In some embodiments of the formulas described herein (Formula I, I-A, I-B, I-B-1, I-A-1 to I-A-9, or I-A-1' to I-A-9'), $X_2$ can be $CL_2R_3$, wherein $L_2$ and $R_3$ are as defined herein. In particular, $L_2$ is a linker and $R_3$ is selected from a metal (for e.g., Zn) chelating group, an acid group, or acid isostere. In some embodiments or the formulas disclosed herein, $X_2$ can be $CR_4$, wherein $R_4$ is as defined herein. In some embodiments, $X_2$ can be N. In some embodiments, $X_2$ can be CH.

In some embodiments of the formulas described herein (Formula I, I-A, I-B, I-B-1, I-A-1 to I-A-9, or I-A-1' to I-A-9'), $X_3$ can be $CL_2R_3$, wherein $L_2$ and $R_3$ are as defined herein. In particular, $L_2$ is a linker and $R_3$ is selected from a metal (for e.g., Zn) chelating group, an acid group, or acid isostere. In some embodiments of the formulas, $X_3$ can be $CR_4$, wherein $R_4$ is as defined herein. In some embodiments of the formulas, $X_3$ can be N. In some embodiments of the formulas, $X_3$ can be CH.

In some embodiments of the formulas described herein (Formula I, I-A, I-B, I-B-1, I-A-1 to I-A-9, or I-A-1' to I-A-9'), $X_4$ can be $CL_2R_3$, wherein $L_2$ and $R_3$ are as defined herein. In particular, $L_2$ is a linker and $R_3$ is selected from a metal (for e.g., Zn) chelating group, an acid group, or acid isostere. In some embodiments, $X_4$ can be $CR_4$, wherein $R_4$ is as defined herein. In some embodiments, $X_4$ can be N. In some embodiments, $X_4$ can be CH.

In some embodiments of the formulas described herein (Formula I, I-A, I-B, I-B-1, I-A-1 to I-A-9, or I-A-1' to I-A-9'), $X_5$ can be $CL_2R_3$, wherein $L_2$ and $R_3$ are as defined herein. In particular, $L_2$ is a linker and $R_3$ is selected from a metal (for e.g., Zn) chelating group, an acid group, or acid isostere. In some embodiments, $X_5$ can be $CR_4$, wherein $R_4$ is as defined herein. In some embodiments, $X_5$ can be N. In some embodiments, $X_5$ can be CH.

In some embodiments of the formulas described herein (Formula I, I-A, I-B, I-B-1, I-A-1 to I-A-9, or I-A-1' to I-A-9'), $X_2$ can be $CL_2R_3$ and $X_3$, $X_4$, and $X_5$ can be independently selected from CH, $CL_2R_3$, $CR_4$, or N. In some embodiments, $X_2$ can be $CL_2R_3$ and $X_3$, $X_4$, and $X_5$ can be independently selected from CH, $CR_4$ or N. In some embodiments, $X_2$ can be $CL_2R_3$ and $X_3$, $X_4$, and $X_5$ can be independently selected from CH, $CL_2R_3$ or N. In some embodiments, $X_2$ can be $CL_2R_3$ and $X_3$, $X_4$, and $X_5$ can be CH or $CR_4$. In some examples, $X_2$, $X_3$, and $X_5$ can be CH. In some examples, $X_2$ and $X_3$ can be CH.

In some embodiments of the formulas described herein (Formula I, I-A, I-B, I-B-1, I-A-1 to I-A-9, or I-A-1' to I-A-9'), $X_3$ can be $CL_2R_3$ and $X_2$, $X_4$, and $X_5$ can be independently selected from CH, $CL_2R_3$, $CR_4$, or N. In some embodiments, $X_3$ can be $CL_2R_3$ and $X_2$, $X_4$, and $X_5$ can be independently selected from CH, $CR_4$ or N. In some embodiments $X_3$ can be $CL_2R_3$ and $X_2$, $X_4$, and $X_5$ can be independently selected from CH, $CL_2R_3$ or N. In some embodiments, $X_3$ can be $CL_2R_3$ and $X_2$, $X_4$, and $X_5$ can be CH or $CR_4$.

In some embodiments the formulas described herein (Formula I, I-A, I-B, I-B-1, I-A-1 to I-A-9, or I-A-1' to I-A-9'), $X_4$ can be $CL_2R_3$ and $X_2$, $X_3$, and $X_5$ can be independently selected from CH, $CL_2R_3$, $CR_4$, or N. In some embodiments, $X_4$ can be $CL_2R_3$ and $X_2$, $X_3$, and $X_5$ can be independently selected from CH, $CR_4$ or N. In some embodiments, $X_4$ can be $CL_2R_3$ and $X_2$, $X_3$, and $X_5$ can be independently selected from CH, $CL_2R_3$ or N. In some embodiments, $X_4$ can be $CL_2R_3$ and $X_2$, $X_3$, and $X_5$ can be CH or $CR_4$.

In some embodiments the formulas described herein (Formula I, I-A, I-B, I-B-1, I-A-1 to I-A-9, or I-A-1' to I-A-9'), $X_5$ can be $CL_2R_3$ and $X_2$, $X_3$, and $X_4$ can be independently selected from CH, $CL_2R_3$, $CR_4$, or N. In some embodiments, $X_5$ can be $CL_2R_3$ and $X_2$, $X_3$, and $X_4$ can be independently selected from CH, $CR_4$ or N. In some embodiments, $X_5$ can be $CL_2R_3$ and $X_2$, $X_3$, and $X_4$ can be independently selected from CH, $CL_2R_3$ or N. In some embodiments, $X_5$ can be $CL_2R_3$ and $X_2$, $X_3$, and $X_4$ can be CH or $CR_4$.

As described herein, $L_1$ is a linker. In some embodiments of the formulas described herein (Formula I, I-A, I-B, I-B-1, I-A-1 to I-A-9, or I-A-1' to I-A-9'), $L_1$ can be selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring. $L_1$ can be optionally substituted with one or more groups. In some examples, $L_1$ can be a bond, —$C_1$-$C_3$ alkylene, —$C_1$-$C_3$ alkoxy-, or —$C_1$-$C_3$ alkylamide-. For example, $L_1$ can be —$C_1$-$C_3$ alkylene, such as methylene, ethylene, or propylene. In some examples, $L_1$ can be —$C_1$-$C_3$ alkoxy-, such as methoxy, ethoxy, or propoxy. In some examples, $L_1$ can be —$C_1$-$C_3$ alkylamide. In some examples, $L_1$ can be a bond.

As described herein, $L_2$ is a linker. In some embodiments of the formulas described herein (Formula I, I-A, I-B, I-B-1, I-A-1 to I-A-9, or I-A-1' to I-A-9'), $L_2$ can be selected from a bond, —$C_1$-$C_6$ alkylene-, —$C_2$-$C_6$ alkenylene-, —$C_2$-$C_6$ alkynylene-, —$C_1$-$C_6$ haloalkylene-, —$C_2$-$C_6$ haloalkenylene-, —$C_2$-$C_6$ haloalkynylene-, —$C_1$-$C_6$ alkoxy-, —$C_1$-$C_6$ alkenyleneoxy-, —$C_1$-$C_6$ alkylamine-, —$C_1$-$C_6$ alkylamide-, —$C_1$-$C_6$ alkylsulfide-, —$C_1$-$C_6$ alkylthiol-, —$C_1$-$C_6$ alkylsulfoxide-, —$C_1$-$C_6$ alkylsulfonyl-, —$C_1$-$C_6$ alkylsulfonamide-, —$C_1$-$C_6$ alkylsulfoximine-, —$C_1$-$C_6$ alkyl sulfur diimide-, —$C_3$-$C_7$ cycloalkyl-, —$C_2$-$C_7$ heterocycloalkyl-, —$C_5$-$C_7$ aryl-, —$C_2$-$C_7$ heteroaryl-, —R'$CO_2$R"—, —C(O)R"—, —R'CONHR"—, —R'CONR"R'"—, wherein R', R", and R" are independently absent or selected from a bond, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, aryl, alkylaryl, heteroaryl or two or more of R', R", and R'" can combine and form a ring. $L_2$ can be optionally substituted with one or more groups. In some examples, $L_2$ can be a bond, —$C_1$-$C_3$ alkylene, —$C_1$-$C_3$ alkoxy-, or —$C_1$-$C_3$ alkylamide-. For example, $L_2$ can be —$C_1$-$C_3$ alkylene, such as methylene, ethylene, or propylene. In some examples, $L_2$ can be —$C_1$-$C_3$ alkoxy-, such as methoxy, ethoxy, or propoxy. In some examples, $L_2$ can be —$C_1$-$C_3$ alkylamide. In some examples, $L_2$ can be a bond.

In some embodiments of the formulas described herein (Formula I, I-A, I-B, I-B-1, I-A-1 to I-A-9, or I-A-1' to I-A-9'), $R_1$ can be hydrogen. In some examples, both $R_1$ and $R_5$ can be hydrogen. In some embodiments, $R_1$ can be a $C_1$-$C_6$ alkyl (methyl, ethyl, propyl, butyl, pentyl, or hexyl), a $C_1$-$C_4$ alkyl, or a $C_1$-$C_2$ alkyl. In some embodiments, $R_1$ can be a $C_1$-$C_6$ alkoxy (methoxy, ethoxy, or propoxy), a $C_1$-$C_4$ alkoxy, or a $C_1$-$C_2$ alkoxy. In some embodiments, $R_1$ can be a $C_1$-$C_6$haloalkyl (fluoromethyl, trifluoromethyl, or trifluoroethyl), a $C_1$-$C_4$ haloalkyl, or a $C_1$-$C_2$haloalkyl.

In some embodiments of the formulas described herein (Formula I, I-A, I-B, I-B-1, I-A-1 to I-A-9, or I-A-1' to I-A-9'), $R_2$ can be selected from aryl (e.g., $C_6$-$C_{10}$ aryl) or heteroaryl (e.g., $C_2$-$C_8$ heteroaryl). For example, $R_2$ can be selected from phenyl, benzodioxole, or pyridinyl. Examples of other heteroaryl groups include piridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. The aryl or heteroaryl rings can be unsubstituted or substituted by one or more moieties as described herein. for example, $R_2$ can be optionally substituted with one or more groups selected from halogen, alkyl, haloalkyl, alkoxy, haloalkoxy, amine, alkylamine, amide, alkylamide, alkyl heterocycloalkyl, hydroxyl, cyano, nitro, ester, ether, $SF_5$, or haloalkyl. In some examples, $R_2$ can be optionally substituted with one or more alkoxy groups, alkyl heterocycloalkyl, or a combination thereof.

In some embodiments of the formulas described herein (Formula I, I-A, I-B, I-B-1, I-A-1 to I-A-9, or I-A-1' to I-A-9'), $R_3$ can be selected from a metal (for e.g., Zn) chelating group, an acid group, or an acid isostere. For example, $R_3$ can be selected from —CONHR", —ONH—C(O)R", —C(O)N($CH_2$R")—OR'", —NHCONHCO—R", —$SO_2$NR", —N$SO_2$R", —CONH$SO_2$R", —CONH$SO_2$NR"R'", —$PO_2$HR", —$PO_3$R", substituted or unsubstituted heterocycloalkyl, substituted or unsubstituted heterocycloalkenyl, substituted or unsubstituted aryl, or substituted or unsubstituted heteroaryl, wherein R" and R'" are independently selected from hydrogen, $C_1$-$C_6$ alkyl, $C_1$-$C_6$ haloalkyl, substituted or unsubstituted cycloalkyl, substituted or unsubstituted heterocycloalkyl, substituted or unsubstituted heterocycloalkenyl, substituted or unsubstituted cycloalkenyl, substituted or unsubstituted aryl, or substituted or unsubstituted heteroaryl or two or more of R', R", and R'" can combine and form a ring. In some examples, R" and R'" are independently selected from hydrogen or $C_1$-$C_6$ alkyl.

In some embodiments of the formulas described herein (Formula I, I-A, I-B, I-B-1, I-A-1 to I-A-9, or I-A-1' to I-A-9'), $R_3$ can be selected from halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, —R'COR", —COR", —SR", —SO—R", —$SO_2$—R", —R'$SO_3$R", —$SO_3$R", cycloalkyl, or cycloalkenyl, wherein R', R", and R'" are independently selected from hydrogen, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, cycloalkyl, alkyl cycloalkyl, cycloalkenyl, alkyl cycloalkenyl, heterocycloalkyl, alkyl heterocycloalkyl, cycloheteroalkenyl, substituted or unsubstituted aryl, alkylaryl, substituted or unsubstituted heteroaryl, alkylheteroaryl or two or more of R', R", and R'" can combine and form a ring, and wherein $R_3$ is optionally substituted with one or more groups.

As described herein, in some embodiments of the formulas described herein (Formula I, I-A, I-B, I-B-1, I-A-1 to I-A-9, or I-A-1' to I-A-9'), $X_4$ can be $CL_2R_3$, wherein C is defined as a carbon atom. In the formula $CL_2R_3$, $L_2R_3$ can be selected from —CONHR", —CONHOR", —C(OH)R", —ONH—C(O)R", —C(O)N($CH_2$R")—OR'", —C(O)N $(CH_3)$—OR''', —$CH_2$—C(O)N($CH_3$)—OR''', —NHCONHCO—R'', —$SO_2NH_2$, —$SO_2NR''$, —$NHSO_2R''$, —$CONHSO_2R''$, —$CONHSO_2NR''R'''$, —C(O)haloalkyl, —C(O)alkyl, —R''C(O)alkyl, —$PO_2H_2$, —$PO_2HR''$, —$PO_3H'$, —$PO_3R''$, —SR'', —SOR'', —$SO_2H$, —$SO_2R''$, —$SO_3H$, —$SO_3R''$, substituted cycloalkenyl, substituted or unsubstituted dioxocyclopentyl, substituted or unsubstituted heterocycloalkyl, substituted or unsubstituted heterocycloalkenyl, substituted or unsubstituted aryl, or substituted or unsubstituted heteroaryl, wherein R'' and R''' are independently selected from $C_1$-$C_6$ alkyl, $C_1$-$C_6$ haloalkyl, substituted or unsubstituted cycloalkyl, substituted or unsubstituted heterocycloalkyl, substituted or unsubstituted heterocycloalkenyl, substituted or unsubstituted cycloalkenyl, substituted or unsubstituted aryl, or substituted or unsubstituted heteroaryl. Preferably, $X_4$ is $CL_2R_3$, wherein $L_2R_3$ is selected from —CONHR'', —CONHOR'', —C(OH)R'', —ONH—C(O)R'', —C(O)N($CH_2R''$)—OR''', —C(O)N($CH_3$)—OR''', —$CH_2$—C(O)N($CH_3$)—OR''', —NHCONHCO—R'', —$SO_2NH_2$, —$SO_2NR''$, —$NHSO_2R''$, —$CONHSO_2R''$, —$CONHSO_2NR''R'''$, —C(O)haloalkyl, —C(O)alkyl, —R''C(O)alkyl, —$PO_2HR''$, —$PO_3R''$, —SR'', —SOR'', —$SO_2R''$, —$SO_3R''$, substituted cycloalkenyl, substituted or unsubstituted dioxocyclopentyl, substituted or unsubstituted heterocycloalkyl, substituted or unsubstituted heterocycloalkenyl, substituted or unsubstituted aryl, or substituted or unsubstituted heteroaryl, wherein R'' and R''' are independently selected from substituted or unsubstituted cycloalkyl, substituted or unsubstituted heterocycloalkyl, substituted or unsubstituted heterocycloalkenyl, substituted or unsubstituted cycloalkenyl, substituted or unsubstituted aryl, or substituted or unsubstituted heteroaryl.

In some embodiments of the formulas described herein (Formula I, I-A, I-B, I-B-1, I-A-1 to I-A-9, or I-A-1' to I-A-9'), $R_4$ can be hydrogen. In some embodiments, $R_4$ can be a $C_1$-$C_6$ alkyl (methyl, ethyl, propyl, butyl, pentyl, or hexyl), a $C_1$-$C_4$ alkyl, or a $C_1$-$C_2$ alkyl. In some embodiments, $R_4$ can be a $C_1$-$C_6$ alkoxy (methoxy, ethoxy, or propoxy), a $C_1$-$C_4$ alkoxy, or a $C_1$-$C_2$ alkoxy. In some embodiments, $R_4$ can be a $C_1$-$C_6$ haloalkyl (fluromethyl, triflurometheyl, or trifluoroethyl), a $C_1$-$C_4$ haloalkyl, or a $C_1$-$C_2$haloalkyl.

In some embodiments of the formulas described herein (Formula I, I-A, I-B, I-B-1, I-A-1 to I-A-9, or I-A-1' to I-A-9'), $R_5$ can be hydrogen. In some embodiments, $R_5$ can be a $C_1$-$C_6$ alkyl (methyl, ethyl, propyl, butyl, pentyl, or hexyl), a $C_1$-$C_4$ alkyl, or a $C_1$-$C_2$ alkyl. In some embodiments, $R_5$ can be a $C_1$-$C_6$ alkoxy (methoxy, ethoxy, or propoxy), a $C_1$-$C_4$ alkoxy, or a $C_1$-$C_2$ alkoxy. In some embodiments, $R_5$ can be a $C_1$-$C_6$ haloalkyl (flurometheyl, triflurometheyl, or trifluoroethyl), a $C_1$-$C_4$ haloalkyl, or a $C_1$-$C_2$haloalkyl.

In some embodiments of the formulas described herein, the compound can have a structure below:

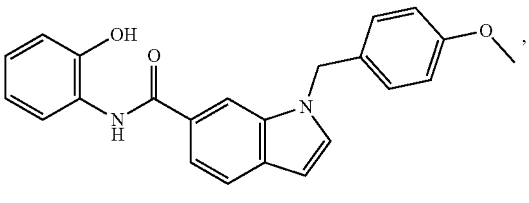,

-continued

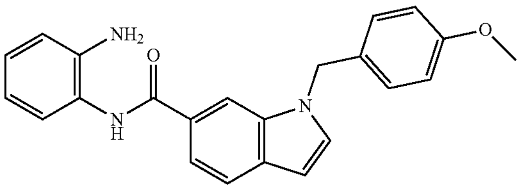,

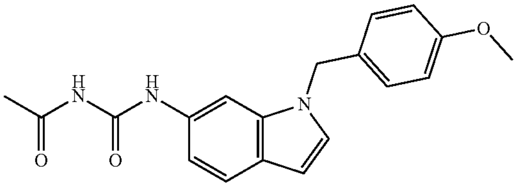,

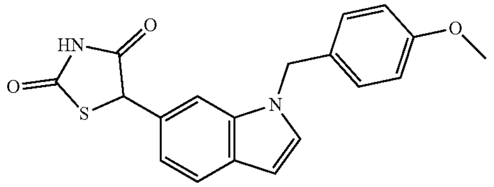,

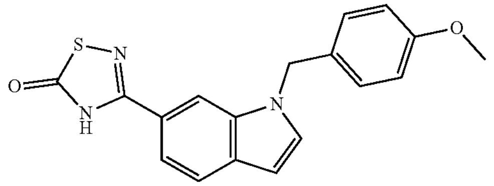,

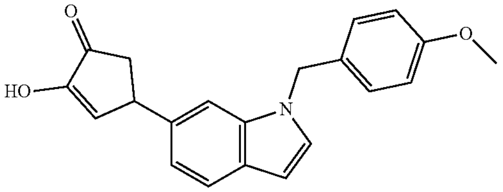,

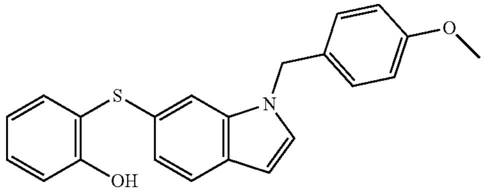,

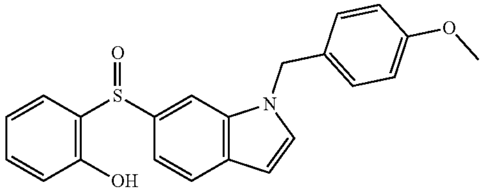,

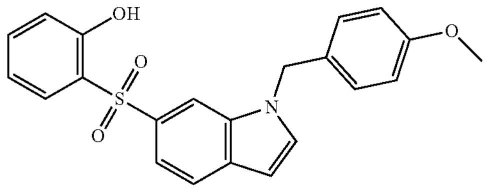,

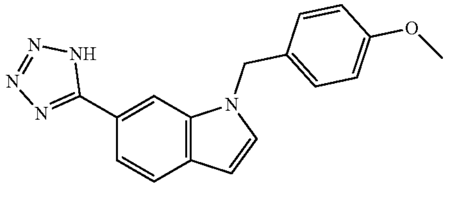,

-continued
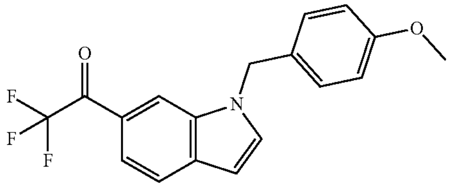,
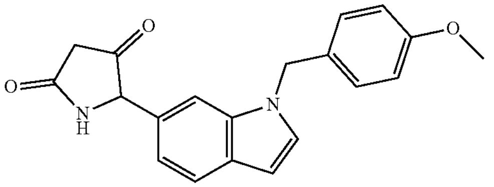,
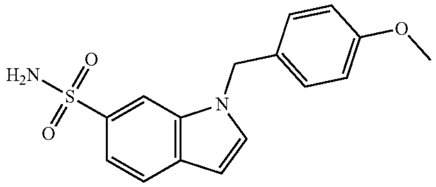,
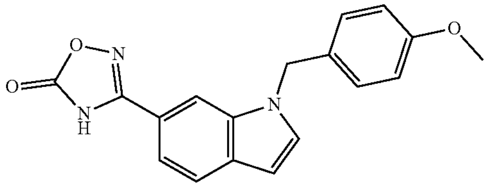,
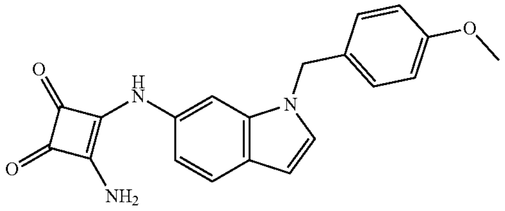,
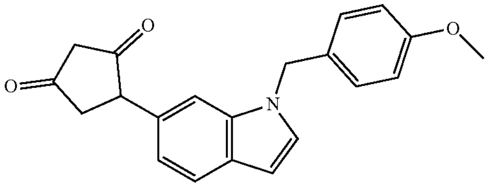,
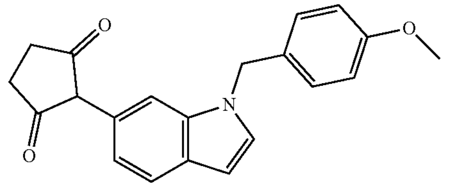,
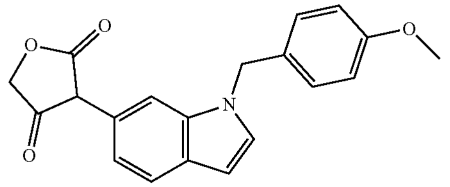,
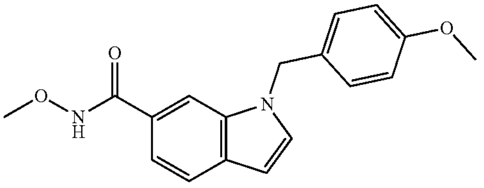,
-continued
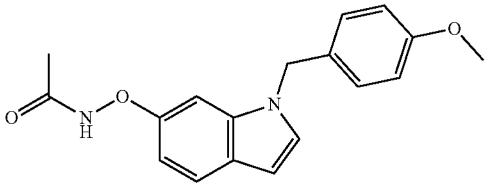,
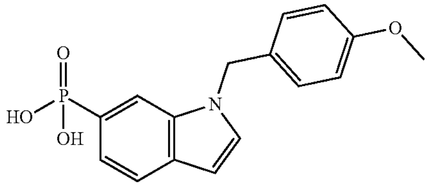,
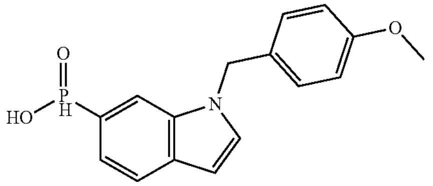,
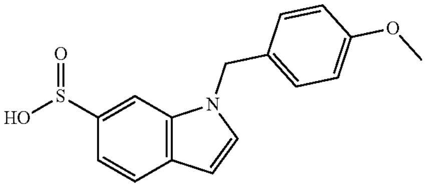,
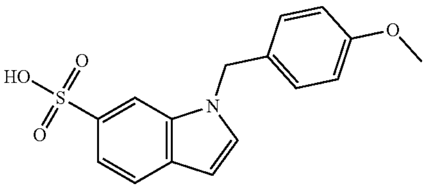,
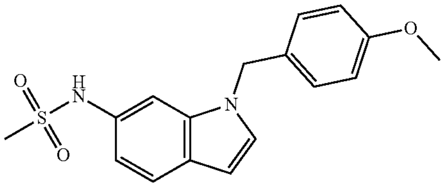,
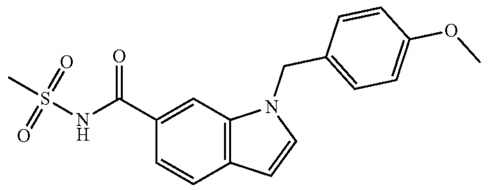,
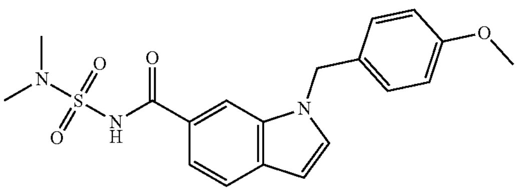,
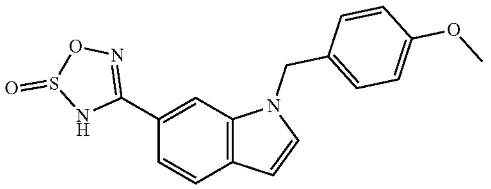, -continued
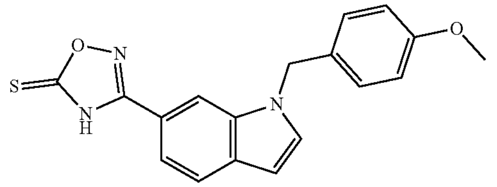
,
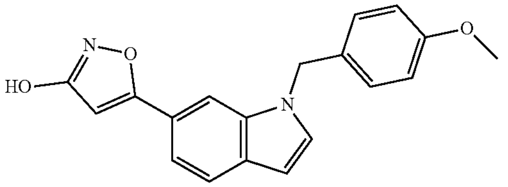
,
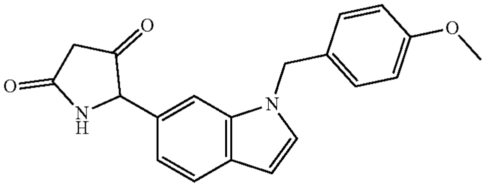
,
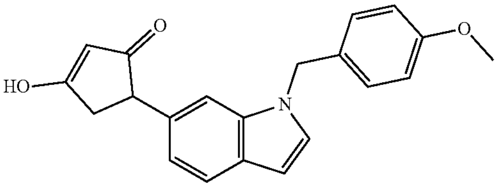
,
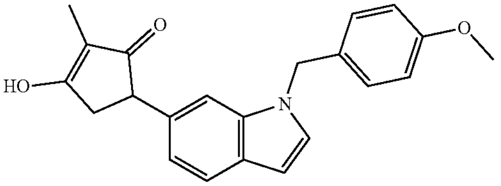
,
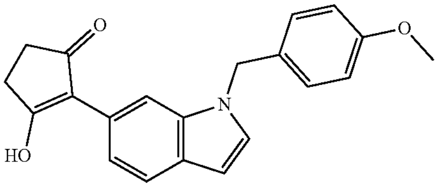
,
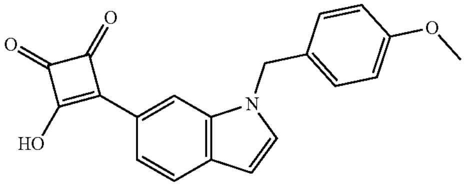
,
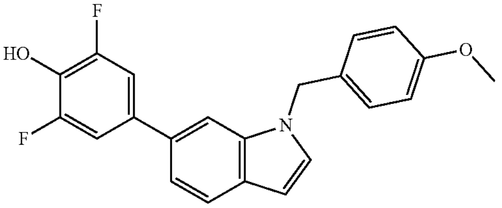
,
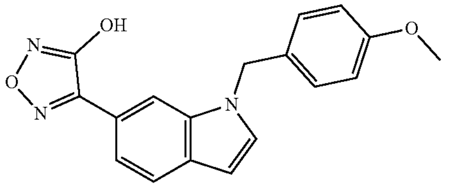
,
-continued
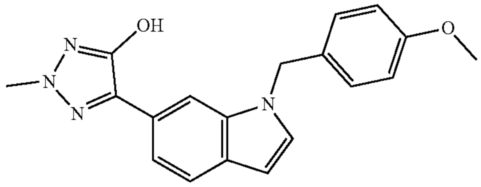
,
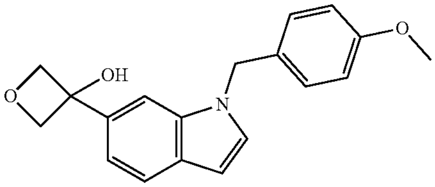
,
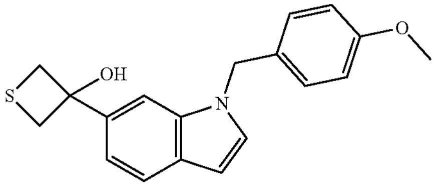
,
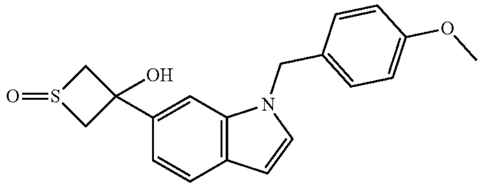
,
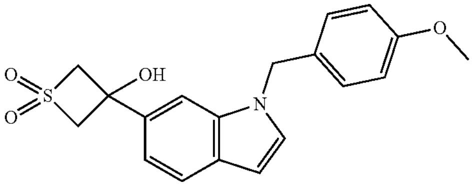
,
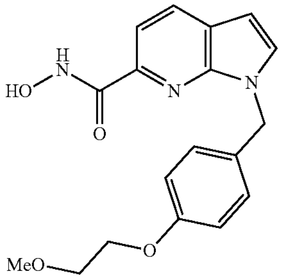
,
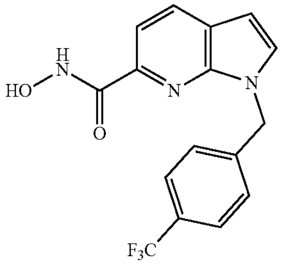
,
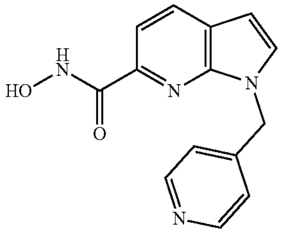
, -continued

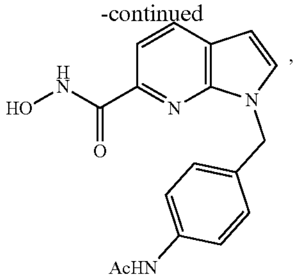,

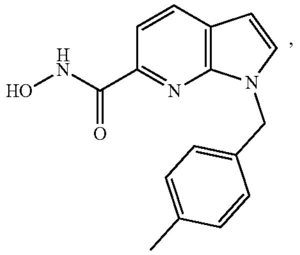,

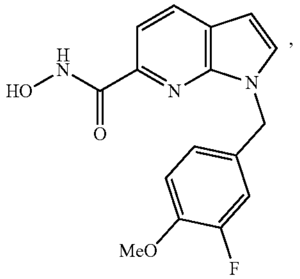,

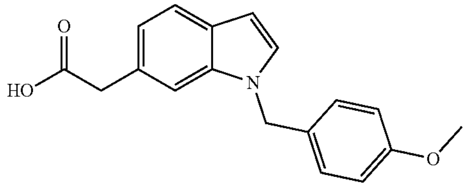,

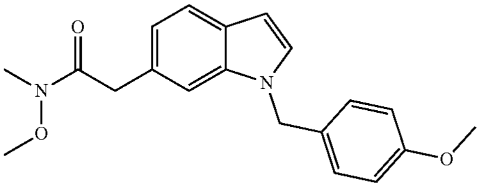,

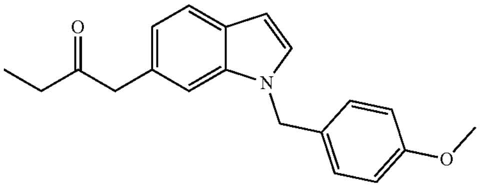,

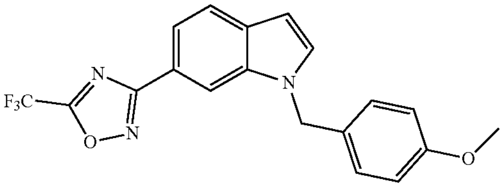

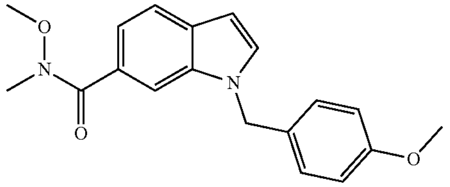,

-continued

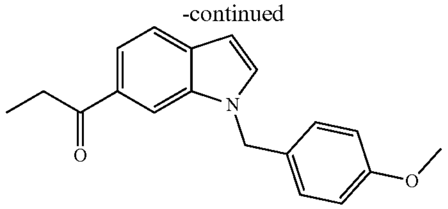,

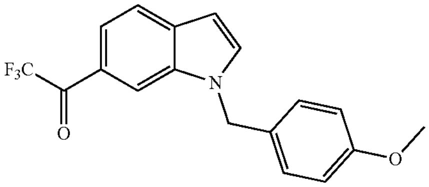,

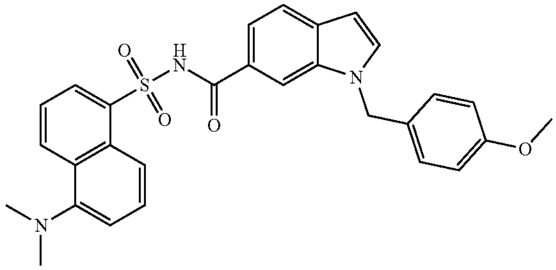,

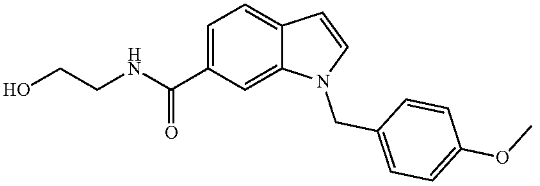,

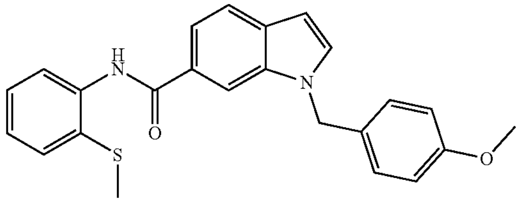, or

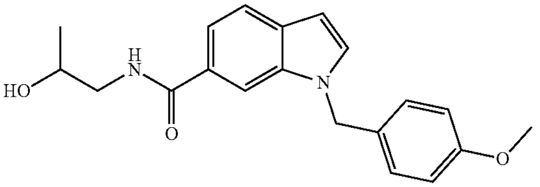.

The compounds disclosed herein exhibit improved bioavailability compared to UHPP-123 for example, which results in more stable, and less variable, absorption of the compounds from the gastrointestinal tract and thereby also a reduction of the required dose of the compound. As known to a person of skill in the art, an increase in drug bioavailability is defined as an increase in the Area Under the Curve (AUC); being the integrated measure of systemic drug concentrations over time, in units of mass-time/volume. The AUC from time zero (the time of dosing) to time infinity (when no drug remains in the body) following the administration of a drug dose is a measure of the exposure of the patient to the drug.

The inventors of the present disclosure have surprisingly found that administration of the disclosed compounds resulted in significantly higher AIUC and $C_{max}$ values such as by 5 fold or greater, 10 fold or greater, 15 fold or greater, or 20 fold or greater, as compared to UHPP-00123, (as further described herein below) attesting to the increase in the oral bioavailability of compounds. Specifically, Tables 1 and 4 show the mean blood pharmacokinetic parameters of UPHH-123 and UPHH-171, respectively, following a single intraperitoneal dose administration to male CD1 mice (Dose: 10.4 and 52 mg/kg). A single dose of 10 mg/kg of the disclosed compounds can cause a 100 fold or greater, 200 fold or greater, or 300 fold or greater increase in compound in the blood, as determined by AUC. A single dose of 50 mg/kg of the disclosed compounds can cause a 100 fold or greater, 200 fold or greater, or 250 fold or greater increase in compound in the blood, as determined by AUC. Comparative Tmax and Cmax data are also shown in Tables 1 and 4. The improvement in bioavailability may be attributed to the change in log P and/or solubility of the disclosed compounds.

Methods of Use

The compounds disclosed herein can be used for preventing or treating renal injury in a subject, the method comprising administering to the subject, a therapeutic effective amount of a compound disclosed herein. In particular embodiments, the method is directed to protecting a kidney from acute renal injury or from chronic renal injury. The renal injury can be associated with the pre-existence in the subject of one or more known risk factors for prerenal, intrinsic renal, or postrenal acute renal failure. In some examples, the renal injury can be associated with exertional rhabdomyolysis, dehydration, a crush-injury, blood loss, burn, sepsis, or an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, injury to renal function, reduced renal function, or acute renal failure, or based on undergoing or having undergone major vascular surgery, coronary artery bypass, or other cardiac surgery, or based on exposure to a nephrotoxic agent such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

The methods of preventing and treating renal injury can comprise further administering to the subject an additional therapeutically active co-agent used in the treatment of renal injury.

Another embodiment of the invention is a method of preventing or treating a subject having an infectious disease. The method can comprise administering to the subject, a therapeutic effective amount of a compound disclosed herein. The infectious disease can be associated with a microbial infection. For example, the infectious disease can be associated with a bacterial infection, a parasitic infection, a viral infection, or a fungal infection.

The methods of preventing and treating infectious diseases can comprise further administering to the subject an additional therapeutically active co-agent used in the treatment of infectious diseases.

Another embodiment of the invention is a method of treating a subject having cancer. The disclosed compounds can exert anticancer effects due to inhibition of histone deacetylases (HDACs). The method of use can comprise administering to the subject, a therapeutic effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Kaposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pine blastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

Administration

The term "administration" and variants thereof (e.g., "administering" a compound) in reference to a compound disclosed herein means introducing the compound or a prodrug of the compound into the system of the animal in need of treatment. When a compound or prodrug thereof is provided in combination with one or more other active agents, "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

For the treatment of the diseases or disorders disclosed herein, compounds and agents and compositions disclosed herein can be administered to a patient in need of treatment prior to, subsequent to, or in combination with other active agents that can treat the diseases or disorders.

Dosage

Appropriate dosage levels on the order of about 0.001 mg to about 5,000 mg per kilogram body weight of the compound active agent may be useful in the treatment of the diseases, disorders, and conditions contemplated herein. Typically, this effective amount of the active agent will generally comprise from about 0.001 mg to about 100 mg per kilogram of patient body weight per day. Moreover, it will be understood that this dosage of active agent can be administered in a single or multiple dosage units to provide the desired therapeutic effect.

The therapeutically effective dosage can be the amount of a compound of the present subject matter required to obtain a serum, in a concentration of 1 nM to 200 uM: 1 nM to 100 uM; 1 nM to 50 uM; 100 nM to 100 uM; 100 nM to 50 uM; 100 nM to 20 uM; 1 nM to 1 uM; and 1 nM to 100 nM. In one embodiment, the compound can be provided at a concentration of less than 200 uM; less than 100 uM; less than 50 uM; less than 25 uM; less than 15 uM; less than 10 uM; less than 5 uM; less than 2 uM; less than 1 uM; less than 500 nM; less than 200 nM; or less than 100 nM.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The compounds or pharmaceutical compositions can be given in a single or multiple doses daily. In an embodiment, the compounds or pharmaceutical compositions are given from one to three times daily. Starting with a low dose twice daily and slowly working up to higher doses if needed is a strategy. The amount of compounds or pharmaceutically active ingredients that may be combined with the carrier materials to produce a single dosage form will vary depending upon the host treated, the nature of the disease, disorder, or condition, and the nature of the active ingredients. It is understood, however, that a specific dose level for any particular patient will vary depending upon a variety of factors, including the activity of the specific pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal pharmaceutical formulations will be determined by one skilled in the art depending upon considerations such as the particular pharmaceutically active agent combination and the desired dosage. See, for example, “Remington’s Pharmaceutical Sciences”, 18th ed. (1990, Mack Publishing Co., Easton, Pa. 18042), pp. 1435-1712, the disclosure of which is hereby incorporated by reference.

Such formulations may influence the physical state, stability, rate of in vivo release, and rate of in vivo clearance of the essential lipids.

In an embodiment, the present compounds or pharmaceutical composition in accordance with the subject matter described herein may be an intravenous form or an oral dosage form, for example, a capsule, a tablet, liquid, and/or a powder packaged in, for example, a multi-use or single-use package, including for example, a container or bottle, a blister package.

Single dosage kits and packages containing once per day, or once per treatment, amount of the compounds or pharmaceutical composition may be prepared. Single dose, unit dose, and once-daily disposable containers of the present compounds or pharmaceutical compositions are contemplated as within the scope of the present subject matter.

Combination Therapy

As described herein, the present compounds or pharmaceutical compositions may be used in combination with an additional pharmaceutical dosage form to enhance their effectiveness for treating renal injury, infectious diseases, or cancer. In this regard, the present preferred compositions may be administered as part of a regimen additionally including any other pharmaceutical and/or pharmaceutical dosage form known in the art as effective for the treatment of the specific conditions disclosed herein. Similarly, a pharmaceutically active ingredient other than those specified herein can be added to the present preferred compositions to enhance their effectiveness in treating the condition. Accordingly, this additional pharmaceutically active ingredient or additional pharmaceutical dosage form can be administered to a patient either directly or indirectly, and concomitantly or sequentially, with the preferred compositions described herein.

In one embodiment, the present compounds or compositions and the additional pharmaceutical dosage form can be administered to a patient at the same time. In an alternative embodiment, one of the present preferred compounds or compositions and the additional pharmaceutical dosage form can be administered in the morning and the other can be administered in the evening.

In another embodiment, the presently described compounds can be administered to a patient in need thereof in multiple pharmaceutical dosage forms. This combination therapy may maximize the effectiveness of the present composition in treating a specific disorder.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

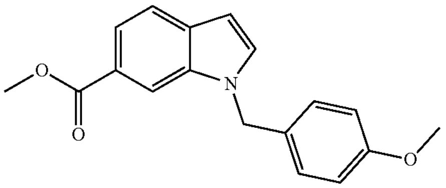

Methyl 1-(4-methoxybenzyl)-1H-indole-6-carboxylate: To a solution of methyl 1H-indole-6-carboxylate (700 mg) in MeCN (30 mL) stirred in an ice bath was added 60% NaH (270 mg) after washing with hexanes. Bubbles formed upon addition. The reaction was stirred in an ice bath for 30 minutes. 1-(chloromethyl)-4-methoxybenzene (0.8 mL) was added drop wise to the solution, and the reaction was raised from the ice bath and stirred at room temperature overnight. The reaction was quenched with saturated $NH_4Cl$ solution (15 mL) and diluted with EtOAc (150 mL). The organic layers were washed with water (15 mL) and brine (15 mL) and collected. The organic layers were dried over $Na_2SO_4$, filtered, and concentrated to give crude product. Crude product was purified on silica gel column chromatography (0-15% EtOAc in Hexanes) to give 850 mg of an amber solid (72%).

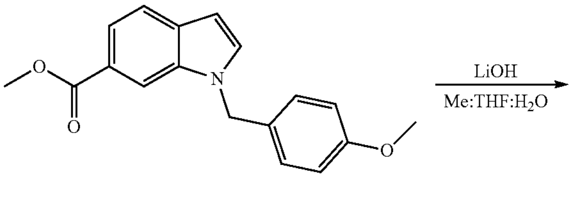

-continued

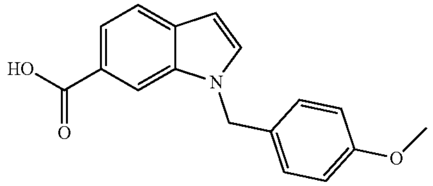

1-(4-methoxybenzyl)-1H-indole-6-carboxylic acid

To a solution of 400 mg of methyl 1-(4-methoxybenzyl)-1H-indole-6-carboxylate (1.35 mmol) in a 1:1:1 solution of MeOH:THF:$H_2O$ (6 mL) that had been cooled in an ice bath was added LiOH (130 mg, 5.40 mmol). The reaction mixture was allowed to warm to room temperature and stirred for 16 hours, then diluted with EtOAc (5 mL) and quenched with 4 M HCl until the pH reached approximately 5. After addition of EtOAc (20 mL), the organic phase was separated, and extracted with $H_2O$ (5 mL), dried over $Na_2SO_4$, filtered, and concentrated under reduced pressure. The crude product was purified on silica column chromatography (0-50% EtOAc/hexanes) to afford 1-(4-methoxybenzyl)-1H-indole-6-carboxylic acid (326 mg, 86%) as a yellow solid. $^1H$ NMR (600 MHz, $CDCl_3$) δ 8.18 (s, 1H), 7.85 (d, J=8.3 Hz, 1H), 7.68 (d, J=8.3 Hz, 1H), 7.28 (d, J=3.4 Hz, 1H), 7.10 (d, J=8.6 Hz, 2H), 6.85 (d, J=8.6 Hz, 2H) 6.59 (d, J=2.8 Hz, 1H), 5.33 (s, 2H), 3.78 (s, 3H).

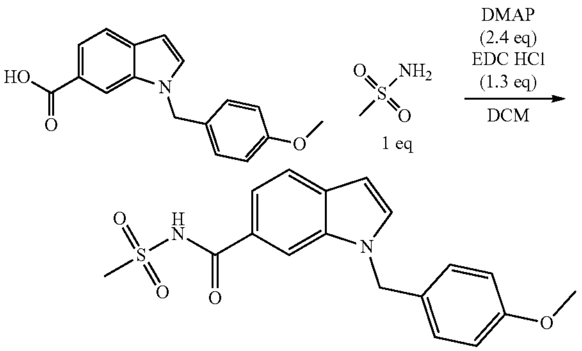

UPHH-00171

1-(4-methoxybenzyl)-N-(methylsulfonyl)-1H-indole-6-carboxamide (UPHH-00171)

To a solution of EDC HCl (664 mg, 3.47 mmol) in DCM (15 mL) was added DMAP (782 mg, 6.40 mmol). This mixture was stirred at room temperature until DMAP dissolved. On cooling in an ice bath, 1-(4-methoxybenzyl)-1H-indole-6-carboxylic acid (750 mg, 2.67 mmol) and methanesulfonamide (254 mg, 2.67 mmol) were added, and the reaction was stirred for 16 hours after warming to room temperature, then quenched with 1 N HCl until the pH reached 1. The reaction mixture was diluted with DCM (10 mL), the organic phase was separated, extracted with saturated $NH_4Cl$ solution (10 mL), dried over $Na_2SO_4$, filtered, and concentrated under reduced pressure. The crude product was purified on silica column chromatography (0-15% EtOAc/DCM) to afford 1-(4-methoxybenzyl)-N-(methylsulfonyl)-1H-indole-6-carboxamide (600 mg, 63%) as an off white solid. $^1H$ NMR (600 MHz, DMSO) δ 8.29 (s, 1H), 7.72 (d, J=3.0 Hz, 1H), 7.64 (s, 2H), 7.20 (d, J=8.6 Hz, 2H), 6.89 (d, J=8.6 Hz, 2H), 6.58 (d, J=2.9 Hz, 1H), 5.42 (s, 2H), 3.70 (s, 3H), 3.39 (s, 3H). $^{13}C$ NMR (151 MHz, $CDCl_3$) δ 165.98, 159.39, 135.72, 133.05, 132.39, 128.43, 128.24, 123.77, 121.35, 117.95, 114.37, 110.93, 102.31, 55.31, 49.86, 41.85.

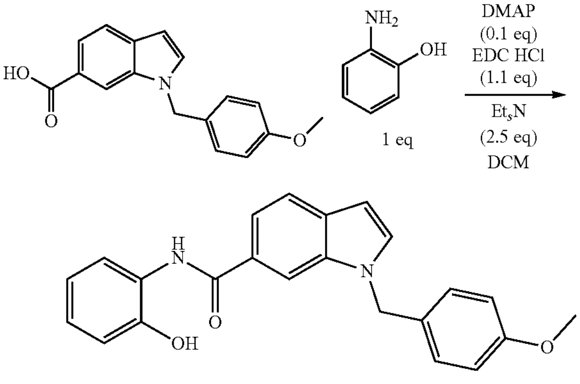

UPHH-00172

N-(2-hydroxyphenyl)-1-(4-methoxybenzyl)-1H-indole-6-carboxamide (UPHH-00172)

To a solution of 1-(4-methoxybenzyl)-1H-indole-6-carboxylic acid (60 mg, 0.213 mmol) in DCM (3 mL) that had been cooled in an ice bath was added DMAP (2.8 mg, 0.021 mmol), 2-aminophenol (30.7 mg, 0.276 mmol) and $Et_3N$ (0.08 mL, 0.534 mmol). EDC HCl (36 mg, 0.188 mmol) was added and the reaction stirred in an ice bath for 1 hour. The reaction mixture was allowed to warm to room temperature and stirred for 16 hours, then diluted with EtOAc (20 mL), extracted with 1N HCl (3 mL) and saturated $NaHCO_3$ solution (3 mL), dried over $Na_2SO_4$, filtered, and concentrated under reduced pressure. The crude product was purified on silica column chromatography (0-60% EtOAc/hexanes) to afford N-(2-hydroxyphenyl)-1-(4-methoxybenzyl)-1H-indole-6-carboxamide (15 mg, 19%) as a brown solid. $^1H$ NMR (600 MHz, $CDCl_3$) δ 9.14 (s, 1H), 8.12 (s, 1H), 8.07 (s, 1H), 7.75 (d, J=8.3 Hz, 1H), 7.56 (d, J=8.4 Hz, 1H), 7.19 (t, J=7.1 Hz, 1H), 7.12-7.10 (m, 4H), 6.94 (t, J=6.8 Hz, 1H), 6.87 (d, J=8.6 Hz, 2H), 6.63 (d, J=3.0 Hz, 1H), 5.37 (s, 2H), 3.80 (s, 3H). $^{13}C$ NMR (151 MHz, $CDCl_3$) δ 168.20, 159.38, 149.22, 135.97, 132.10, 131.58, 128.67, 128.38, 127.28, 125.92, 122.39, 121.17, 120.46, 120.26, 117.42, 114.33, 110.76, 102.13, 55.31, 49.82.

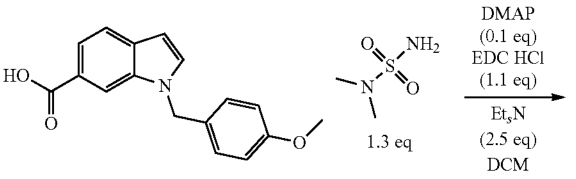

-continued

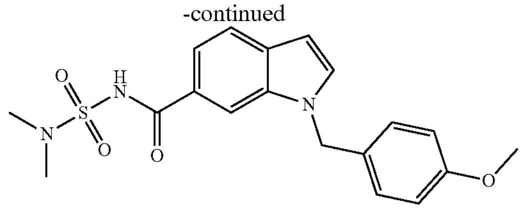

UPHH-00173

N—(N,N-dimethylsulfamoyl)-1-(4-methoxybenzyl)-1H-indole-6-carboxamide (UPHH-00173)

To a solution of 1-(4-methoxybenzyl)-1H-indole-6-carboxylic acid (60 mg, 0.213 mmol) in DCM (3 mL) that was cooled in an ice bath was added DMAP (2.8 mg, 0.021 mmol). N,N-dimethylsulfamide (30.7 mg, 0.276 mmol) and $Et_3N$ (0.08 mL, 0.534 mmol). EDC HCl (36 mg, 0.188 mmol) was added and the reaction stirred in an ice bath for 1 hour, then warmed to room temperature and stirred for 16 hours, at which point the mixture was diluted with EtOAc (20 mL), extracted with 3 mL 1 N HCl (3 mL), saturated $NaHCO_3$ solution (3 mL), and brine (3 mL). The organic phase was dried over $Na_2SO_4$, filtered, and concentrated under reduced pressure. The crude product was purified on silica column chromatography (0-30% EtOAc/hexanes) to afford N—(N,N-dimethylsulfamoyl)-1-(4-methoxybenzyl)-1H-indole-6-carboxamide (17 mg, 21%) as an off white solid. $^1H$ NMR (600 MHz, $CDCl_3$) δ 8.45 (s, 1H), 7.95 (s, 1H), 7.69 (d, J=8.3 Hz, 1H), 7.45 (d, J=8.3 Hz, 1H), 7.30 (d, J=3.1 Hz, 1H), 7.06 (d, J=8.6 Hz, 2H), 6.84 (d, J=8.6 Hz, 2H), 6.60 (d, J=2.9 Hz, 1H), 5.32 (s, 2H), 3.78 (s, 3H), 3.05 (s, 6H). $^{13}C$ NMR (151 MHz, $CDCl_3$) δ 165.70, 159.36, 135.80, 132.69, 132.07, 128.50, 128.26, 124.18, 121.24, 117.78, 114.35, 110.73, 102.25, 55.31, 49.76, 38.43, 29.71.

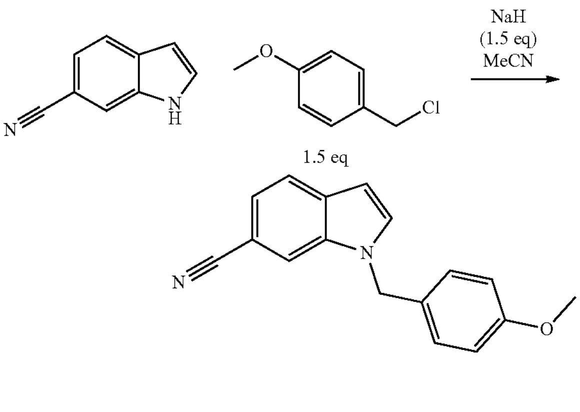

1-(4-methoxybenzyl)-1H-indole-6-carbonitrile

To a stirred solution of methyl 1H-indole-6-carbonitrile (350 mg, 2.46 mmol) in dry acetonitrile (30 mL) under argon that had been cooled in an ice bath was added NaH (3.69 mmol; prepared from washing 152 mg of 60% NaH in mineral oil with hexanes) as a slurry in dry acetonitrile (10 mL). The mixture was allowed to stir for 30 minutes while cooling in an ice bath during which time gas evolved, after which, 1-(chloromethyl)-4-methoxybenzene (578 mg, 3.69 mmol) was added dropwise. The reaction mixture was stirred at room temperature for 16 hours, then was quenched with saturated $NH_4Cl$ solution (15 mL). After dilution with EtOAc (150 mL), the separated organic phase was extracted with $H_2O$ (15 mL) and brine (15 mL), dried over $Na_2SO_4$, filtered, and concentrated under reduced pressure. The crude product was purified on silica column chromatography (0-10% EtOAc/hexanes) to afford 1-(4-methoxybenzyl)-1H-indole-6-carbonitrile (574 mg, 89%) as a white solid. $^1H$ NMR (600 MHz, $CDCl_3$) δ 7.70 (d, J=8.2 Hz, 1H), 7.64 (s, 1H), 7.35-7.33 (m, 2H), 7.08 (d, J=8.5 Hz, 2H), 6.88 (d, J=8.6 Hz, 2H), 6.61 (d, J=2.9 Hz, 1H), 5.30 (s, 2H), 3.81 (s, 3H).

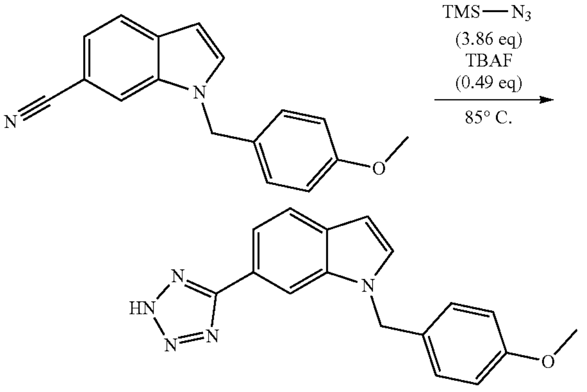

UPHH-00174

1-(4-methoxybenzyl)-6-(2H-tetrazol-5-yl)-1H-indole (UPHH-00174)

Trimethylsilyl azide (0.125 mL, 0.957 mmol), 1-(4-methoxybenzyl)-1H-indole-6-carbonitrile (65 mg, 0.248 mmol) and 1M TBAF in THF (0.12 mL, 0.12 mmol) were combined under an argon atmosphere, and the reaction was heated in an 85° C. bath for 4 hours. The reaction mixture was diluted with EtOAc (20 mL), and extracted with 1 N HCl (4 mL) and brine (4 mL), dried over $Na_2SO_4$, filtered, and concentrated under reduced pressure. The crude product was purified on silica column chromatography (0-20% EtOAc/hexanes) to afford 1-(4-methoxybenzyl)-6-(2H-tetrazol-5-yl)-1H-indole (15 mg, 20%) as an off white solid. $^1H$ NMR (600 MHz, DMSO) δ 8.20 (s, 1H), 7.75 (d, J=8.2 Hz, 1H), 7.70-7.68 (m, 2H), 7.22, (d, J=8.6 Hz, 2H), 6.89 (d, J=8.7 Hz, 2H), 6.59 (d, J=2.9 Hz, 1H), 5.44 (s, 2H), 3.69 (s, 3H). $^{13}C$ NMR (151 MHz, DMSO) δ 158.60, 135.35, 131.82, 130.40, 129.73, 128.40, 121.36, 117.78, 113.98, 109.15, 101.45, 55.01, 48.69.

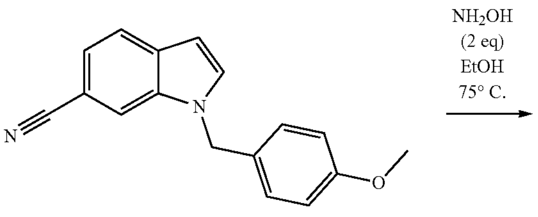

-continued

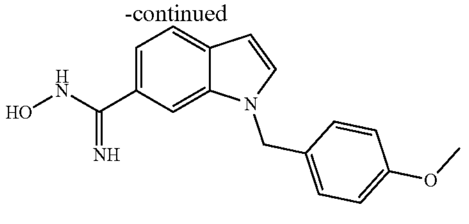

N-hydroxy-1-(4-methoxybenzyl)-1H-indole-6-carboximidamide

A solution of 1-(4-methoxybenzyl)-1H-indole-6-carbonitrile (134 mg, 0.5 mmol) in EtOH (0.5 mL) and 50% hydroxylamine in $H_2O$ (0.132 mL, 1 mmol) and was stirred in a sealed tube in a 75° C. bath for 5 hours. The solvent was evaporated under reduced pressure, and the crude product was purified on silica column chromatography (0-70% EtOAc/hexanes) to afford 1-(4-methoxybenzyl)-6-(2H-tetrazol-5-yl)-1H-indole (95 mg, 64%) as a yellow solid. $^1H$ NMR (600 MHz, $CDCl_3$) δ 7.65 (d, J=8.3 Hz, 1H), 7.63 (s, 1H), 7.36 (d, J=8.2 Hz, 1H), 7.16 (d, J=3.1 Hz, 1H), 7.06 (d, J=8.6 Hz, 2H), 6.83 (d, J=8.6 Hz, 2H), 6.54 (d, J=2.8 Hz, 1H), 5.28 (s, 2H), 4.87 (bs, 2H), 3.78 (s, 3H).

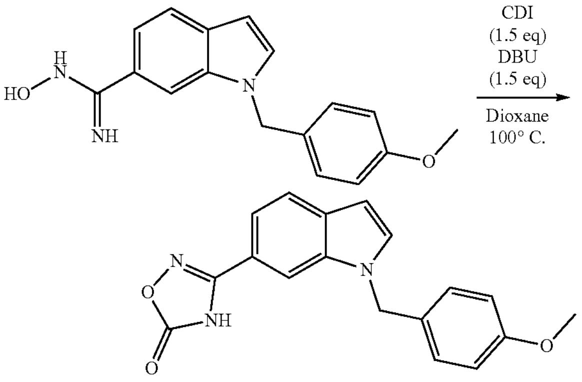

UPHH-00175

3-(1-(4-methoxybenzyl)-1H-indol-6-yl)-1,2,4-oxadiazol-5(4H)-one (UPHH-00175)

To a solution of N-hydroxy-1-(4-methoxybenzyl)-1H-indole-6-carboximidamide (60 mg, 0.203 mmol) in dioxane (8 mL) was added CDI (50 mg, 0.305 mmol) and DBU (50 μL, 0.305 mmol). The reaction was stirred in a 100° C. bath for 1 hour, then quenched with saturated $NH_4Cl$ solution (8 mL) and diluted with EtOAc (20 mL). The organic phase was extracted with brine (8 mL), dried over $Na_2SO_4$, filtered, and concentrated under reduced pressure. The crude product was purified on silica column chromatography (0-50% EtOAc/hexanes) to afford 3-(1-(4-methoxybenzyl)-1H-indol-6-yl)-1,2,4-oxadiazol-5(4H)-one (18 mg, 28%) as an amber solid. $^1H$ NMR (600 MHz, DMSO) δ 12.86 (s, 1H), 8.01 (s, 1H), 7.73 (d, J=2.9 Hz, 1H), 7.72 (d, J=8.3 Hz, 1H), 7.46 (d, J=8.2 Hz, 1H), 7.22 (d, J=8.5 Hz, 2H), 6.88 (d, J=8.5 Hz, 2H), 6.59 (d, J=2.7 Hz, 1H), 5.39 (s, 2H), 3.70 (s, 3H). $^{13}C$ NMR (151 MHz, DMSO) δ 160.09, 158.64, 158.28, 134.97, 132.18, 130.95, 129.62, 128.50, 121.28, 116.39, 115.64, 113.97, 108.60, 101.65, 55.02, 48.68.

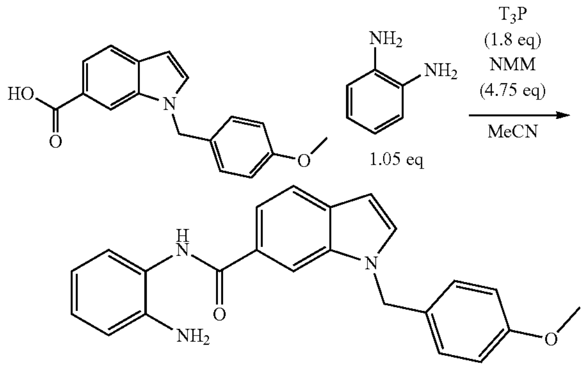

UPHH-00176

N-(2-aminophenyl)-1-(4-methoxybenzyl)-1H-indole-6-carboxamide (UPHH-00176)

To a solution of 1-(4-methoxybenzyl)-1H-indole-6-carboxylic acid (100 mg, 0.355 mmol) in acetonitrile (8 mL) was added 50% propanephosphonic acid anhydride in THF (0.4 mL, 0.628 mmol) and N-methylmorpholine (0.19 mL, 1.69 mmol). After 10 minutes, benzene-1,2-diamine (40 mg, 0.373 mmol) was added, and the reaction was stirred at room temperature for 16 hours. The reaction was diluted with DCM (10 mL), and the reaction mixture was extracted with saturated $NH_4Cl$ solution (2 mL) and $H_2O$ (2 mL), dried over $Na_2SO_4$, filtered, and concentrated under reduced pressure. The crude product was purified on column chromatography (60% EtOAc/hexanes) to afford N-(2-aminophenyl)-1-(4-methoxybenzyl)-1H-indole-6-carboxamide (27 mg, 20%) as a white solid. $^1H$ NMR (600 MHz, $CDCl_3$) δ 8.04 (s, 1H), 7.85 (bs, 1H), 7.71 (d, J=8.2 Hz, 1H), 7.58 (d, J=8.2 Hz, 1H), 7.33 (d, J=6.8 Hz, 1H), 7.10-7.08 (m, J=3.6 Hz, 3H), 6.85 (q, J=6.7 Hz, 4H), 6.59 (d, J=2.9 Hz, 1H), 5.33 (s, 2H), 3.93 (bs, 2H), 3.78 (s, 3H). $^{13}C$ NMR (151 MHz, $CDCl_3$) δ 159.26, 140.72, 135.95, 131.58, 131.07, 128.84, 128.36, 127.31, 127.01, 125.14, 124.94, 120.94, 119.74, 118.34, 117.66, 114.28, 110.37, 101.96, 55.29, 49.75.

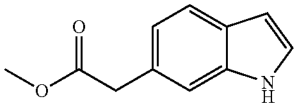

Methyl 2-(1H-indol-6-yl)acetate

To a solution of 2-(1H-indol-6-yl)acetic acid (98 mg) in DMF (2 mL) stirred in an ice bath was added potassium carbonate (103 mg) and iodomethane (0.024 mL). The reaction was raised from the ice bath and stirred at room temperature overnight. DMF was evaporated in vacuo. Reaction was diluted in EtOAc (10 mL) and washed with $H_2O$ (3 mL) and brine (3 mL). The organic layer was dried over $Na_2SO_4$, filtered, and evaporated to give a crude product. Crude product was purified on a silica gel column (0-50% EtOAc in hex) to give 70 mg of an off-white solid (95%).

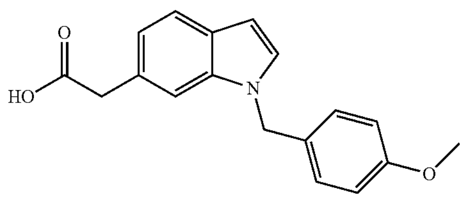 [SMILES: COc1ccc(Cn2ccc3ccc(CC(=O)O)cc32)cc1]

2-(1-(4-methoxybenzyl)-1H-indol-6-yl)acetic acid (UPHH-00249)

To a solution of methyl 2-(1H-indol-6-yl)acetate (49 mg) in MeCN (1 mL) cooled in an ice bath was added 39 mg of 60% NaH in MeCN (1 mL) after the NaH was washed twice with hexanes. The reaction was stirred in an ice bath for 30 minutes. 1-(chloromethyl)-4-methoxybenzene (54 microliters) was added dropwise to the solution. The solution was raised from the bath and stirred at room temperature overnight. The reaction was quenched with saturated $NH_4Cl$ solution (2 mL) and diluted with EtOAc (20 mL). The organic layers were washed with water (2 mL) and brine (2 mL) and collected. The organic layers were dried over $Na_2SO_4$, filtered, and concentrated to give crude product. Crude product was purified on silica gel column chromatography (0-15% EtOAc in Hexanes) to give 60 mg of an amber solid (36%).

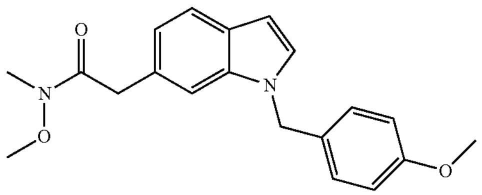

N-methoxy-2-(1-(4-methoxybenzyl)-1H-indol-6-yl)-N-methylacetamide

To a solution of EDC HCl (43.6 mg) in DCM (1 mL) was added DMAP (51.8 mg). The mixture was stirred at room temperature until all solute dissolved. The mixture was cooled in an ice bath and 2-(1-(4-methoxybenzyl)-1H-indol-6-yl)acetic acid (50 mg) as a solution in DCM (1 mL) was added. N, O-dimethylhydroxylamine hydrochloride (17.3 mg) was added and the reaction was raised from the ice bath. The reaction was stirred overnight. The reaction was quenched with $NH_4Cl$ (1 mL) and diluted with DCM (10 mL). The organic layer was washed with brine (5 mL), collected, dried over $Na_2SO_4$, filtered, and concentrated to give crude product. Crude product purified on silica gel column (0-30% EtOAc in Hex) to give 30 mg of amber oil (52%).

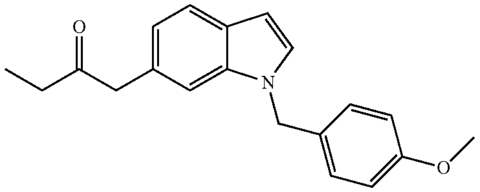 [SMILES: CCC(=O)Cc1ccc2ccn(Cc3ccc(OC)cc3)c2c1]

1-(1-(4-methoxybenzyl)-1H-indol-6-yl)butan-2-one (UPHH-00250)

To a solution cooled in an ice bath of N-methoxy-2-(1-(4-methoxybenzyl)-1H-indol-6-yl)-N-methylacetamide (15 mg) in 1 mL anhydrous THF was added 0.03 mL 3 M EtMgBr solution in ether dropwise. Color turned from yellow to amber. Reaction was monitored by TLC. Reaction was quenched with saturated $NH_4C_1$ solution (1 mL). The aqueous layer was extracted twice with EtOAc (10 mL), washed with brine (5 mL), dried over $Na_2SO_4$, filtered and concentrated to give crude product. Crude product was purified on a silica gel column (0-20% EtOAc in Hex) to give 3 mg of a red-orange oil (18%).

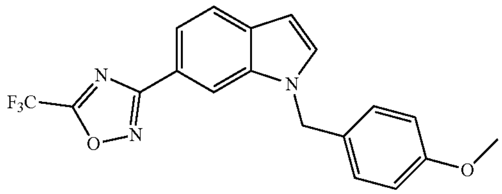 [SMILES: COc1ccc(Cn2ccc3ccc(-c4noc(C(F)(F)F)n4)cc32)cc1]

3-(1-(4-methoxybenzyl)-1H-indol-6-yl)-5-(trifluoromethyl)-1,2,4-oxadiazole (UPHH-00255)

To a solution of N-hydroxy-1-(4-methoxybenzyl)-1H-indole-6-carboximidamide (25 mg) in THF (0.5 mL) stirred in an ice bath was added trifluoromethyl acetic anhydride (0.030 mL). Stirred at room temperature overnight. Reaction was diluted with EtOAc (10 mL) and washed with saturated $NaHCO_3$ solution (2 mL). The organic layer was collected, dried over $Na_2SO_4$, filtered, and concentrated to give crude product. Crude mixture was purified using silica gel column chromatography (0-20% EtOAc in Hex) to give 22 mg of a pale yellow oil (69%).

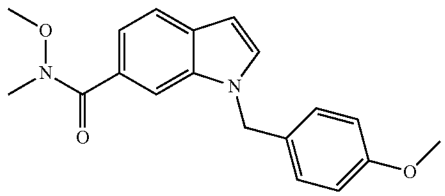

N-methoxy-1-(4-methoxybenzyl)-N-methyl-1H-indole-6-carboxamide

To a solution of 1-(4-methoxybenzyl)-1H-indole-6-carboxylic acid (199.5 mg) in 2 mL anhydrous THF was added 100.5 mg N, O-dimethylhydroxylamine hydrochloride under nitrogen. The reaction was stirred in a −20° C. bath. 2 mL of 1 M Ipr-MgCl was added dropwise. The reaction turned from yellow to amber. The reaction was monitored by TLC. The reaction was quenched with saturated $NH_4Cl$ solution (2 mL). The aqueous layers were extracted twice with EtOAc (10 mL), dried over $Na_2SO_4$, filtered and concentrated to give the crude product. The crude product was purified on a silica gel column (0-80% EtOAc in Hex) to give 165 mg of an amber oil (75%).

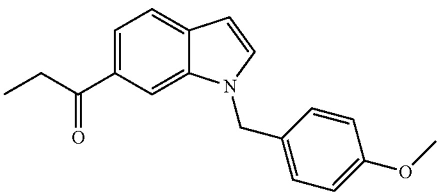 [SMILES: CCC(=O)c1ccc2ccn(Cc3ccc(OC)cc3)c2c1]

1-(1-(4-methoxybenzyl)-1H-indol-6-yl)propan-1-one (UPHH-00235)

To a solution cooled in a ice bath of N-methoxy-1-(4-methoxybenzyl)-N-methyl-1H-indole-6-carboxamide (30 mg) in 1 mL anhydrous THF was added 0.04 mL 3 M EtMgBr solution in ether dropwise. Color turned from yellow to amber. Reaction was monitored by TLC. Reaction was quenched with saturated $NH_4Cl$ solution (1 mL). The aqueous layer was extracted twice with EtOAc (10 mL), washed with brine (5 mL), dried over $Na_2SO_4$, filtered and concentrated to give crude product. Crude product was purified on a silica gel column (0-20% EtOAc in Hex) to give 16 mg of a red-orange solid (59%).

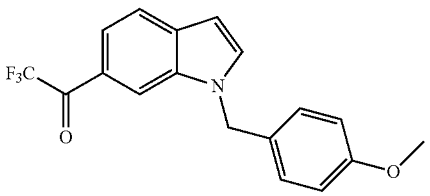 [SMILES: COc1ccc(Cn2ccc3ccc(C(=O)C(F)(F)F)cc32)cc1]

2,2,2-trifluoro-1-(1-(4-methoxybenzyl)-1H-indol-6-yl)ethan-1-one (UPHH-00236)

To a solution of N-methoxy-1-(4-methoxybenzyl)-N-methyl-1H-indole-6-carboxamide (30.3 mg) in toluene (1 mL) was added 4 mg CsF. Reaction was stirred in an ice bath and vented. 0.27 mL of TMS-$CF_3$ was added and the reaction stirred at room temperature. Reaction turned orange. Reaction was monitored by TLC. When starting material disappeared on TLC, Toluene was evaporated under reduced pressure and the crude product was dissolved in THF (0.5 mL). $H_2O$ (0.02 mL) and 1 M TBAF in THF (0.1 mL) was added. Reaction was refluxed for 2 hours. Reaction was monitored by TLC. Reaction was diluted with EtOAc (30 mL) and washed with H2O (5 mL) and brine (5 mL). Organic layer was collected, dried over $Na_2SO_4$, filtered, and concentrated to give the crude product. Crude product was purified on silica gel column (0-5% MeOH in DCM) to give 25 mg of an amber oil (82%).

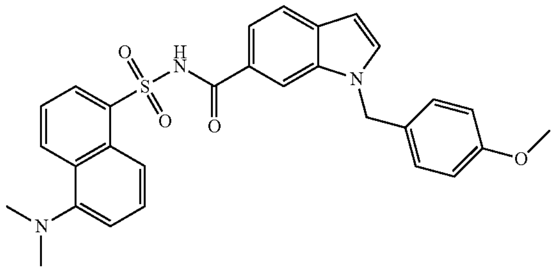

N-((5-(dimethylamino)naphthalen-1-yl)sulfonyl)-1-(4-methoxybenzyl)-1H-indole-6-carboxamide (UPHH-00237)

To a solution of EDC HCl (35.5 mg) in DCM (1 mL) was added DMAP (41.5 mg). Reaction was stirred at room temperature until all solutes dissolved. Reaction was cooled in an ice bath and 1-(4-methoxybenzyl)-1H-indole-6-carboxylic acid (40.6 mg) and Dansyl Amide (35.2 mg) was added. Reaction stirred at room temperature overnight. Reaction went from cloudy to clear. Reaction was monitored by TLC. Reaction was quenched with saturated $NH_4Cl$ solution (2 mL) and acidified with 1 M HCl until pH ~7. Aqueous layer was extracted twice with EtOAc (15 mL), dried over $Na_2SO_4$, filtered, and concentrated to give crude product. Crude product was purified on silica gel column (0-5% MeOH in DCM) to give 65 mg of bright yellow solid (89%).

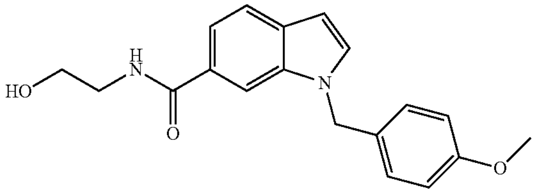 [SMILES: COc1ccc(Cn2ccc3ccc(C(=O)NCCO)cc32)cc1]

N-(2-hydroxyethyl)-1-(4-methoxybenzyl)-1H-indole-6-carboxamide (UPHH-00238)

To a solution of EDC HCl (36.3 mg) in DCM (1 mL) was added DMAP (44 mg). Reaction was stirred at room temperature until all solutes dissolved. Reaction was cooled in an ice bath and 1-(4-methoxybenzyl)-1H-indole-6-carboxylic acid (41 mg) and 2-aminoethan-1-ol (0.08 mL) was added. Reaction stirred at room temperature overnight. Reaction went from cloudy to clear. Reaction was monitored by TLC. Reaction was diluted with $H_2O$ (2 mL) and acidified with 1 M HCl until pH ~2. Aqueous layer was extracted with DCM (20 mL), dried over $Na_2SO_4$, filtered, and concentrated to give crude product. Crude product was purified on silica gel column (0-80% EtOAc in Hex) to give 37 mg of orange solid (80%).

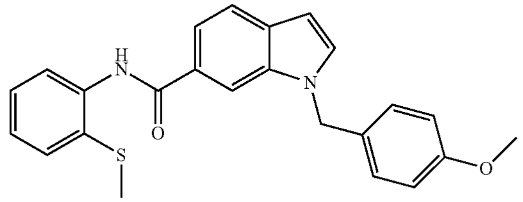 [SMILES: COc1ccc(Cn2ccc3ccc(C(=O)Nc4ccccc4SC)cc32)cc1]

1-(4-methoxybenzyl)-N-(2-(methylthio)phenyl)-1H-indole-6-carboxamide (UPHH-00239)

To a solution of EDC HCl (39.2 mg) in DCM (1 mL) was added DMAP (44.9 mg). Reaction was stirred at room temperature until all solutes dissolved. Reaction was cooled in an ice bath and 1-(4-methoxybenzyl)-1H-indole-6-carboxylic acid (40.2 mg) and 2-(methylthio)aniline (0.017 mL) was added. Reaction stirred at room temperature overnight. Reaction was monitored by TLC. Reaction was diluted with H2O (2 mL) and acidified with 1 M HCl until pH ~1. Aqueous layer was extracted with DCM (20 mL), dried over $Na_2SO_4$, filtered, and concentrated to give crude product. Compound purified on a silica gel column (0-30% EtOAc in Hex) to give 39 mg of a white solid (68%).

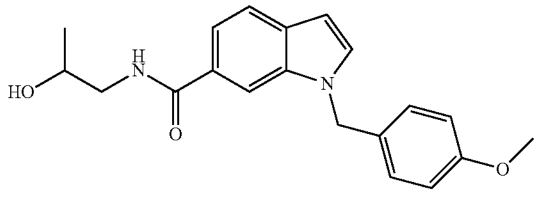 [SMILES: COc1ccc(Cn2ccc3ccc(C(=O)NCC(C)O)cc32)cc1]

N-(2-hydroxypropyl)-1-(4-methoxybenzyl)-1H-indole-6-carboxamide (UPHH-00244)

To a solution of EDC HCl (37.4 mg) in DCM (1 mL) was added DMAP (40.4 mg). Reaction was stirred at room temperature until all solutes dissolved. Reaction was cooled in an ice bath and 1-(4-methoxybenzyl)-1H-indole-6-carboxylic acid (39.7 mg) and 1-aminopropan-2-ol (0.01 mL) was added. Reaction stirred at room temperature overnight. Reaction was monitored by TLC. Reaction was diluted with DCM (10 mL) and washed with water and 1 M HCl until pH was roughly 1. Organic layer was washed with brine (10 mL). Organic layers were collected, dried over $Na_2SO_4$, filtered, and concentrated to give crude product. Crude product was purified on a silica gel column (0-80% EtOAc in hex) to give 37 mg of a yellow oil (77%).

Synthesis of N-hydroxy-1-(4-(2-methoxyethoxy)benzyl)-1H-pyrrolo[2,3-b]pyridine-6-carboxamide (7)

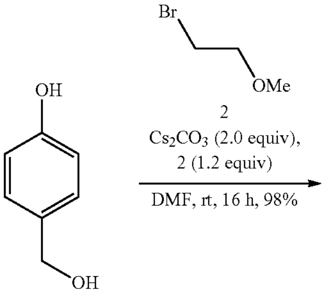

1

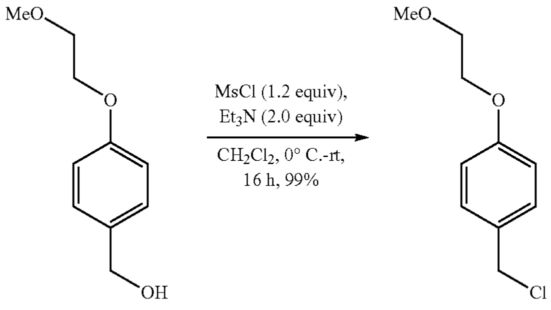

3

4

-continued

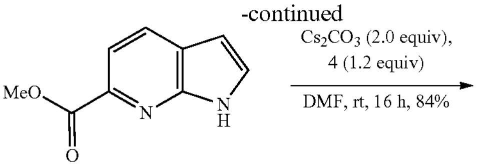

5

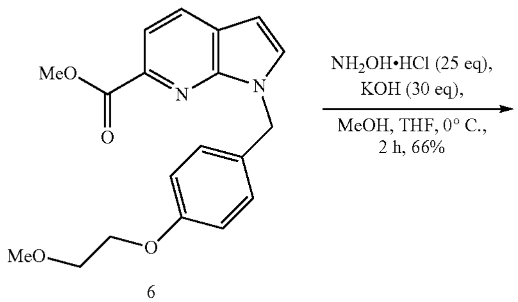

6

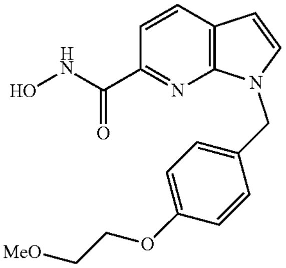

7

Synthesis of (4-(2-methoxyethoxy)phenyl)methanol (3): To a solution of 4-(hydroxymethyl)phenol (1), 1.00 g, 8.05 mmol) in DMF (20 mL) was added cesium carbonate (2.0 equiv, 5.24 g, 16.10 mmol), and 1-bromo-2-methoxyethane (2), (1.2 equiv, 1.34 g, 9.66 mmol). The resulting mixture was stirred at room temperature for 16 h. The reaction mixture was partitioned in ethyl acetate and water. Ethyl acetate layer was separated, and aqueous layer was extracted with ethyl acetate (2×100 mL) and the combined organic layer was washed with water, brine, and dried over sodium sulfate to yield a clear, free-flowing liquid. The residue was purified by column chromatography (20-50% hexanes-ethyl acetate) to yield (4-(2-methoxyethoxy)phenyl)methanol (3) 1.45 g (98%) of a yellow solid. $^1H$ NMR (600 Hz, $CDCl_3$)

δ 7.28 (dt, J=8.4, 2.2 Hz, 2H), 6.91 (dt, J=6.4, 2.4 Hz, 2H), 4.61 (d, J=5.07 Hz, 2H), 4.11 (ddd, J=4.8, 4.6, 3.3 Hz, 2H), 3.75 (ddd, J=6.0, 4.8, 3.3 Hz, 2H), 3.45 (s, 3H), 1.73 (t, J=5.8 Hz, 1H); $^{13}C$ NMR (150 Hz, $CDCl_3$) 158.3, 133.4, 129.3, 128.5, 115.2, 114.6, 71.0, 67.3, 65.0, 59.2 ppm.

Synthesis of 1-(chloromethyl)-4-(2-methoxyethoxy)benzene (4): To a solution of (4-(2-methoxyethoxy)phenyl) methanol (3) (1.40 g, 7.69 mmol) in dry $CH_2Cl_2$ (20 ml) and cooled to 0° C., then $Et_3N$ (2.10 mL, 15.18 mmol) and MsCl (0.71 mL, 9.20 mmol) was added slowly The resulting mixture was brought to room temperature and stirred for 16 h at room temperature. The reaction mixture was diluted with water, then extracted with $CH_2Cl_2$, washed with water and brine, dried over sodium sulfate, filtered, removed the solvent to get 1-(chloromethyl)-4-(2-methoxyethoxy)benzene (4), 1.56 g (>99%) as yellow liquid directly used for the next step without further purification. $^1H$ NMR (600 Hz, $CDCl_3$) δ 7.29 (dt, J=6.4, 2.2 Hz, 2H), 6.89 (dt, J=6.6, 2.2 Hz, 2H), 4.55 (s, 2H), 4.10 (ddd, J=6.1, 4.7, 3.3 Hz, 2H), 3.73 (ddd, J=6.0, 4.5, 2.9 Hz, 2H), 3.43 (s, 3H); $^{13}C$ NMR (150 Hz, $CDCl_3$) 158.7, 129.9, 129.8, 114.6, 70.8, 67.2, 59.1, 46.1 ppm.

Synthesis of methyl 1-(4-(2-methoxyethoxy)benzyl)-1H-pyrrolo[2,3-b]pyridine-6-carboxylate (6): To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by 1-(chloromethyl)-4-(2-methoxyethoxy)benzene (4, 84.0 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 20-40% hexanes-ethyl acetate to get methyl 1-(4-(2-methoxyethoxy)benzyl)-1H-pyrrolo[2,3-b]pyridine-6-carboxylate (6, 120 mg, 84%) as off white solid. $^1H$ NMR (600 Hz, $CDCl_3$) δ 7.98 (q, J=8.2 Hz, 2H), 7.20 (dt, J=6.5, 2.2 Hz, 2H), 7.29 (brs, 1H), 6.87 (dt, J=6.5, 1.9 Hz, 2H), 6.51 (d, J=4.0, Hz, 1H), 5.50 (s, 2H), 4.08 (ddd, J=4.9, 4.4, 3.4 Hz, 2H), 4.01 (s, 3H), 3.43 (s, 3H), 3.73 (ddd, J=6.0, 4.5 3.0 Hz, 2H); $^{13}C$ NMR (150 Hz, $CDCl_3$) 166.8, 158.7, 147.2, 140.7, 131.2, 129.5, 129.4, 128.6, 117.4, 114.8, 100.2, 70.9, 67.2, 59.2, 52.6, 47.4 ppm Synthesis of N-hydroxy-1-(4-(2-methoxyethoxy)benzyl)-1H-pyrrolo[2,3-b]pyridine-6-carboxamide (7): To an ice-cooled solution of hydroxylamine hydrochloride (668 mg, 9.55 mmol) in methanol (10 mL) was added powdered KOH (630 mg, 11.24 mmol) portion wise and the resulting mixture was stirred at room temperature for 1 hour after the addition of KOH was completed. The precipitate was filtered off and the filtrate was added dropwise to an ice-cooled solution of methyl 1-(4-(2-methoxyethoxy)benzyl)-1H-pyrrolo[2,3-b]pyridine-6-carboxylate (6,120 mg, 0.38 mmol) in methanol (5.0 mL). An additional amount of KOH (220 mg, 3.80 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield N-hydroxy-1-(4-(2-methoxyethoxy)benzyl)-1H-pyrrolo[2,3-b]pyridine-6-carboxamide (7) as gray color white solid (86 mg, 66%). $^1H$ NMR (600 Hz, $DMSO_{d6}$) δ 11.47 (s, 1H), 9.08 (d, J=1.4 Hz, 1H), 8.08 (d, J=8.0 Hz, 1H), 7.77 (d, J=3.4 Hz, 1H), 7.74 (d, J=8.0 Hz, 1H), 7.36 (dt, J=8.6, 3.0 Hz, 2H), 6.88 (dt, J=8.6, 3.0 Hz, 2H), 6.55 (d, J=3.4 Hz, 1H), 5.53 (s, 2H), 4.03 (ddd, J=6.0, 4.5, 3.0 Hz, 2H), 3.62 (ddd, J=6.0, 4.6, 3.0 Hz, 2H), 3.28 (s, 3H)$^{13}C$ NMR (150 Hz, $DMSO_{d6}$): 162.3, 157.8, 145.3, 142.6, 131.4, 130.5, 129.4, 129.0, 122.0, 114.3, 113.5, 99.9, 70.3, 66.8, 58.1, 46.2 ppm; HRMS (ESI) m/z [M-H]$^+$ calcd for $C_{18}H_{18}O_4N_3$ 340.1292; found 340.1303.

Synthesis of N-hydroxy-1-(4-(trifluoromethyl)benzyl)-1H-pyrrolo[2,3-b]pyridine-6-carboxamide (10)

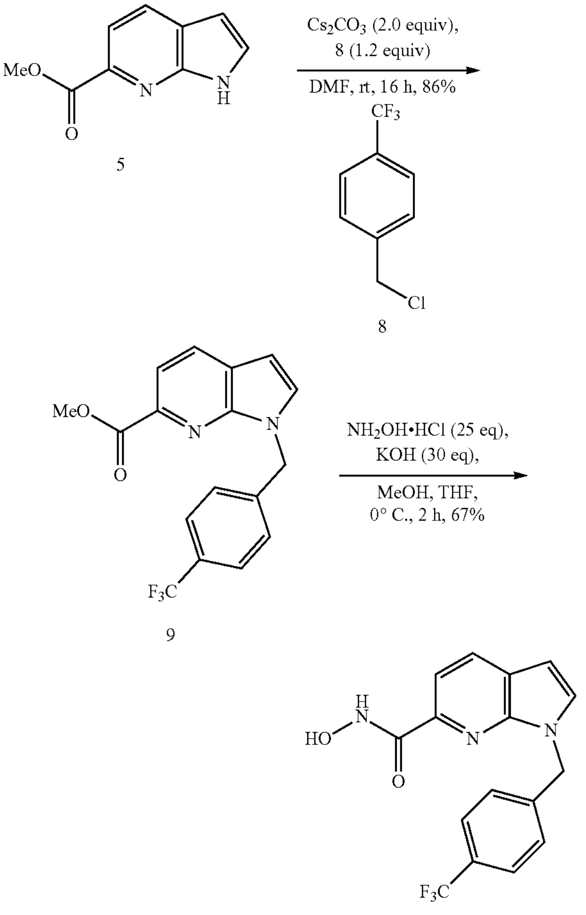

5

8

9

10

Synthesis of methyl 1-(4-(trifluoromethyl)benzyl)-1H-pyrrolo[2,3-b]pyridine-6-carboxylate (9): To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by 1-(chloromethyl)-4-(trifluoromethyl)benzene (8, 82.0 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 20-40% hexanes-ethyl acetate to get methyl 1-(4-(trifluoromethyl)benzyl)-1H-pyrrolo[2,3-b]pyridine-6-carboxylate (9, 120 mg, 86%) as off white solid. $^1$H NMR (600 Hz, $CDCl_3$) δ 8.00 (q, J=8.0 Hz, 2H), 7.55 (d, J=8.0 Hz, 2H), 7.32-7.31 (m, 3H), 6.57 (d, J=3.5 Hz, 1H), 5.63 (s, 2H), 3.99 (s, 3H); $^{13}$C NMR (150 Hz, $CDCl_3$) 166.7, 147.2, 141.4, 141.1, 131.2, 130.3, 130.1, 129.9, 129.7, 127.9, 126.7, 125.7, 125.7, 125.7, 125.6, 124.9, 123.3, 123.1, 121.3, 117.7, 101.0, 52.6, 47.7 ppm.

Synthesis of N-hydroxy-1-(4-(trifluoromethyl)benzyl)-1H-pyrrolo[2,3-b]pyridine-6-carboxamide (10): To an ice-cooled solution of hydroxylamine hydrochloride (668 mg, 9.55 mmol) in methanol (10 mL) was added powdered KOH (630 mg, 11.24 mmol) portion wise and the resulting mixture was stirred at room temperature for 1 hour after the addition of KOH was completed. The precipitate was filtered off and the filtrate was added dropwise to an ice-cooled solution methyl 1-(4-(trifluoromethyl)benzyl)-1H-pyrrolo[2,3-b]pyridine-6-carboxylate (9,120 mg, 0.38 mmol) in methanol (5.0 mL). An additional amount of KOH (220 mg, 3.80 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield N-hydroxy-1-(4-(trifluoromethyl)benzyl)-1H-pyrrolo[2,3-b]pyridine-6-carboxamide (10) as gray color white solid (85 mg, 67%). $^1$H NMR (600 Hz, $DMSO_{d6}$) δ 11.47 (s, 1H), 9.08 (d, J=1.4 Hz, 1H), 8.12 (d, J=7.9 Hz, 1H), 7.83 (d, J=3.4 Hz, 1H), 7.77 (d, J=8.0 Hz, 1H), 7.70 (d, J=8.4 Hz, 1H), 7.54 (d, J=8.1 Hz, 2H), 6.62 (d, J=3.4 Hz, 2H), 5.73 (s, 2H); $^{13}$C NMR (150 Hz, $DMSO_{d6}$): 162.2, 145.5, 143.2, 142.8, 131.6, 129.3, 128.3, 128.1, 127.9, 129.7, 126.9, 125.4, 125.4, 125.4, 125.4, 125.1, 123.3, 122.0, 121.5, 113.8, 100.4, 46.3 ppm; HRMS (ESI) m/z [M-H]$^+$ calcd for $C_{16}H_{11}O_2N_3F_3$ 334. 1292; found 334. 0811.

Synthesis of N-hydroxy-1-(4-(trifluoromethyl)benzyl)-1H-pyrrolo[2,3-b]pyridine-6-carboxamide (13)

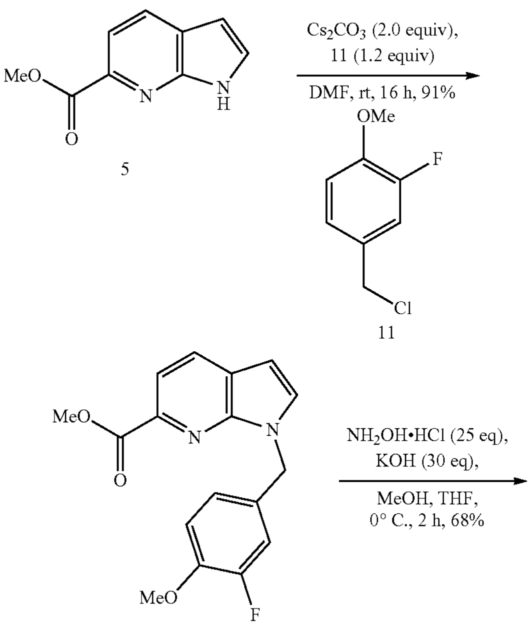

5
11
12

-continued

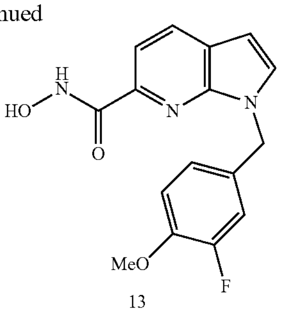
13

Synthesis of methyl 1-(3-fluoro-4-methoxybenzyl)-1H-pyrrolo[2,3-b]pyridine-6-carboxylate (12): To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by 4-(chloromethyl)-2-fluoro-1-methoxybenzene (11, 74.0 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 20-40% hexanes-ethyl acetate to get methyl 1-(3-fluoro-4-methoxybenzyl)-1H-pyrrolo[2,3-b]pyridine-6-carboxylate (12, 120 mg, 91%) as off white solid. $^1$H NMR (600 Hz, $CDCl_3$) δ 7.99 (q, J=8.1 Hz, 2H), 7.31 (d, J=3.6 Hz, 1H), 7.01-6.98 (m, 2H), 6.89 (t, J=9.1 Hz, 1H), 6.54 (d, J=3.3 Hz, 1H), 5.49 (s, 2H), 4.01 (s, 3H), 3.85 (s, 3H); $^{13}$C NMR (150 Hz, $CDCl_3$) 166.8, 153.1, 151.5, 147.1, 140.9, 131.1, 128.8, 123.8, 123.4, 117.6, 115.9, 115.8, 113.4, 113.4, 100.6, 56.2, 52.6, 47.1 ppm.

Synthesis of 1-(3-fluoro-4-methoxybenzyl)-N-hydroxy-1H-pyrrolo[2,3-b]pyridine-6-carboxamide (13): To an ice-cooled solution of hydroxylamine hydrochloride (668 mg, 9.55 mmol) in methanol (10 mL) was added powdered KOH (630 mg, 11.24 mmol) portion wise and the resulting mixture was stirred at room temperature for 1 hour after the addition of KOH was completed. The precipitate was filtered off and the filtrate was added dropwise to an ice-cooled solution methyl 1-(3-fluoro-4-methoxybenzyl)-1H-pyrrolo[2,3-b]pyridine-6-carboxylate (12,120 mg, 0.38 mmol) in methanol (5.0 mL). An additional amount of KOH (220 mg, 3.80 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield 1-(3-fluoro-4-methoxybenzyl)-N-hydroxy-1H-pyrrolo[2,3-b]pyridine-6-carboxamide (11) as gray color white solid (82 mg, 68%). $^1$H NMR (600 Hz, $DMSO_{d6}$) δ 11.51 (d, J=1.6 Hz, 1H), 9.09 (d, J=1.8 Hz, 1H), 8.09 (d, J=8.0 Hz, 1H), 7.83 (d, J=3.7 Hz, 1H), 7.75 (d, J=8.0 Hz, 1H), 7.37 (dd, J=12.4, 2.3 Hz, 1H), 7.23 (dd, J=8.7, 1.3 Hz, 1H), 7.10 (t, J=8.6 Hz, 1H), 6.57 (d, J=3.8 Hz, 1H), 5.52 (s, 2H), 3.78 (s, 3H); $^{13}$C NMR (150 Hz, $DMSO_{d6}$): 162.2, 151.9, 150.3, 146.5, 146.4, 145.3, 142.7, 131.4, 131.2, 131.2, 129.1, 124.5, 124.5, 122.0, 115.9, 115.7, 113.8, 113.8, 113.6, 100.1, 55.9, 45.9, 40.0 ppm; HRMS (ESI) m/z [M-H]$^+$ calcd for $C_{16}H_{13}O_3N_3F$ 314.0935; found 314.0949.

Synthesis of N-hydroxy-1-(pyridin-4-ylmethyl)-1H-pyrrolo[2,3-b]pyridine-6-carboxamide (16)

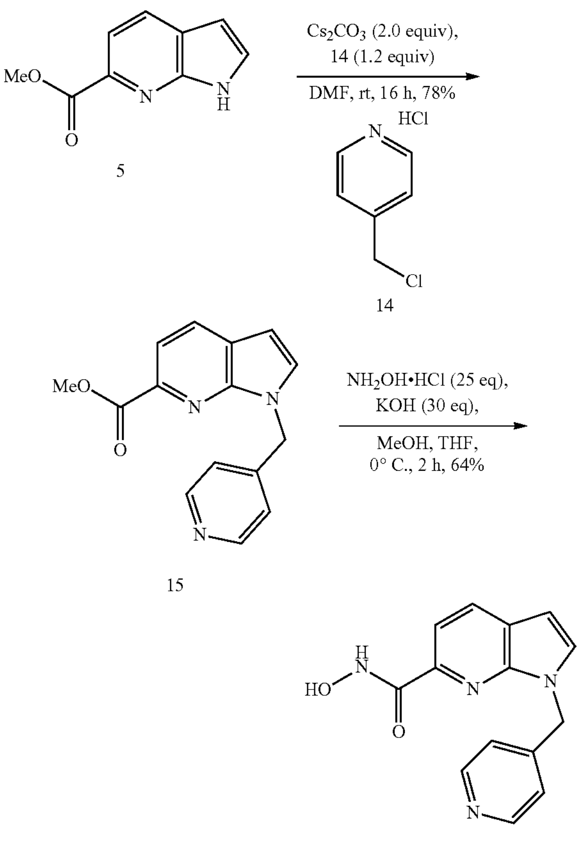

5

14

15

10

Synthesis of methyl 1-(pyridin-4-ylmethyl)-1H-pyrrolo[2,3-b]pyridine-6-carboxylate (15): To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by 4-(chloromethyl)pyridine hydrogen chloride (14, 69.0 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 50-70% hexanes-ethyl acetate to get methyl 1-(pyridin-4-ylmethyl)-1H-pyrrolo[2,3-b]pyridine-6-carboxylate (15, 88.0 mg, 78%) as off white solid. $^1H$ NMR (600 Hz, $CDCl_3$) δ 8.53 (d, J=6.0 Hz, 2H), 8.04 (d, J=8.0 Hz, 1H), 8.00 (d, J=8.0 Hz, 1H), 7.34 (d, J=3.8 Hz, 1H), 7.07 (d, J=6.0 Hz, 2H), 6.61 (d, J=3.6 Hz, 1H), 5.62 (s, 2H), 3.99 (s, 3H); $^{13}C$ NMR (150 Hz, $CDCl_3$) 166.6, 150.2, 150.1, 147.2, 146.4, 141.2, 131.2, 129.1, 123.2, 122.2, 117.8, 101.2, 52.6, 46.8 ppm.

Synthesis of N-hydroxy-1-(pyridin-4-ylmethyl)-1H-pyrrolo[2,3-b]pyridine-6-carboxamide (16): To an ice-cooled solution of hydroxylamine hydrochloride (576 mg, 8.23 mmol) in methanol (10 mL) was added powdered KOH (555 mg, 9.90 mmol) portion wise and the resulting mixture was stirred at room temperature for 1 hour after the addition of KOH was completed. The precipitate was filtered off and the filtrate was added dropwise to an ice-cooled solution methyl 1-(pyridin-4-ylmethyl)-1H-pyrrolo[2,3-b]pyridine-6-carboxylate (15, 88.0 mg, 0.33 mmol) in methanol (5.0 mL). An additional amount of KOH (185 mg, 3.30 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield N-hydroxy-1-(pyridin-4-ylmethyl)-1H-pyrrolo[2,3-b]pyridine-6-carboxamide (16) as a gray color solid (57.0 mg, 64%). $^1H$ NMR (600 Hz, $DMSO_{d6}$) δ 11.44 (s, 1H), 9.07 (s, 1H), 8.50 (d, J=5.6 Hz, 2H), 7.83 (d, J=3.7 Hz, 1H), 8.13 (d, J=8.2 Hz, 1H), 7.82 (d, J=3.4 Hz, 1H), 7.77 (d, J=8.1 Hz, 1H), 7.23 (dt, J=4.6, 1.5 Hz, 1H), 6.64 (d, J=3.5 Hz, 1H), 5.68 (s, 2H); $^{13}C$ NMR (150 Hz, $DMSO_{d6}$): 162.1, 149.8, 147.2, 145.6, 142.9, 131.7, 129.3, 122.3, 121.9, 113.8, 100.5, 45.7 ppm; HRMS (ESI) m/z $[M-H]^+$ calcd for $C_{14}H_{11}O_2N_4$ 267.0877; found 267.0889.

Synthesis of 1-(4-acetamidobenzyl)-N-hydroxy-1H-pyrrolo[2,3-b]pyridine-6-carboxamide (19)

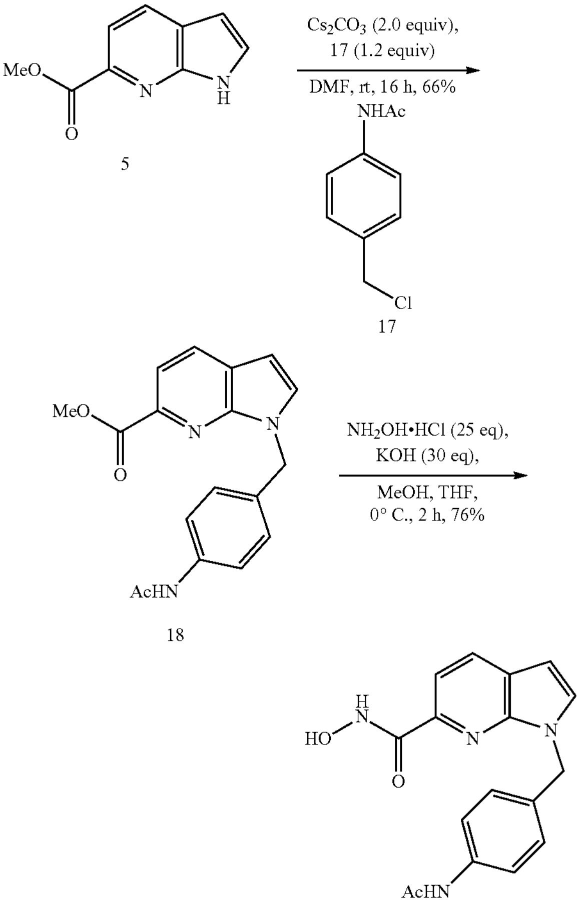

5

17

18

19

Synthesis of methyl 1-(4-acetamidobenzyl)-1H-pyrrolo[2,3-b]pyridine-6-carboxylate (18): To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by N-(4-(chloromethyl)phenyl)acetamide (17, 77.0 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 50-70% hexanes-ethyl acetate to get methyl 1-(4-acetamidobenzyl)-1H-pyrrolo[2,3-b]pyridine-6-carboxylate (18, 90.0 mg, 66%) as off white solid. $^{1}H$ NMR (600 Hz, $CDCl_3$) δ 7.99 (q, J=7.8 Hz, 2H), 7.43 (d, J=8.3 Hz, 2H), 7.30 (d, J=3.6 Hz, 1H), 7.33 (brs, 1H), 7.16 (d, J=8.2 Hz, 2H), 6.53 (d, J=3.6 Hz, 1H), 5.52 (s, 2H), 4.01 (s, 3H), 2.16 (s, 3H); $^{13}C$ NMR (150 Hz, $CDCl_3$) 168.2, 166.8, 147.2, 140.8, 137.5, 133.0, 132.0, 131.4, 128.8, 128.6, 128.6, 123.4, 120.0, 117.5, 52.6, 47.4, 24.6 ppm.

Synthesis of 1-(4-acetamidobenzyl)-N-hydroxy-1H-pyrrolo[2,3-b]pyridine-6-carboxamide (19): To an ice-cooled solution of hydroxylamine hydrochloride (487 mg, 6.96 mmol) in methanol (10 mL) was added powdered KOH (453 mg, 8.10 mmol) portion wise and the resulting mixture was stirred at room temperature for 1 hour after the addition of KOH was completed. The precipitate was filtered off and the filtrate was added dropwise to an ice-cooled solution methyl 1-(4-acetamidobenzyl)-1H-pyrrolo[2,3-b]pyridine-6-carboxylate (18, 90.0 mg, 0.27 mmol) in methanol (5.0 mL). An additional amount of KOH (151 mg, 2.70 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield 1-(4-acetamidobenzyl)-N-hydroxy-1H-pyrrolo[2,3-b]pyridine-6-carboxamide (19) as a gray color solid (67.0 mg, 76%). $^{1}H$ NMR (600 Hz, $DMSO_{d6}$) δ 11.45 (s, 1H), 9.92 (s, 1H), 9.08 (s, 1H), 8.09 (d, J=8.0 Hz, 1H), 7.76-7.74 (m, 2H), 7.50 (d, J=8.0 Hz, 2H), 7.33 (d, J=8.1 Hz, 2H), 6.57 (d, J=2.2 Hz, 1H), 5.54 (s, 2H), 2.01 (s, 3H); $^{13}C$ NMR (150 Hz, $DMSO_{d6}$): 168.1, 162.3, 145.4, 142.6, 138.5, 132.8, 131.4, 129.0, 128.3, 122.0, 118.9, 113.5, 100.0, 48.5, 23.9 ppm; HRMS (ESI) m/z $[M-H]^+$ calcd for $C_{17}H_{15}O_3N_4$ 323.1139; found 323.1150.

Synthesis of N-hydroxy-1-(4-methylbenzyl)-1H-pyrrolo[2,3-b]pyridine-6-carboxamide (22)

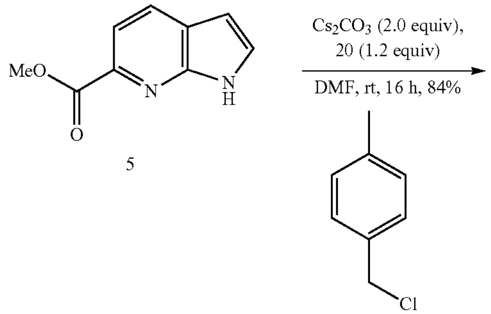

5

20

-continued

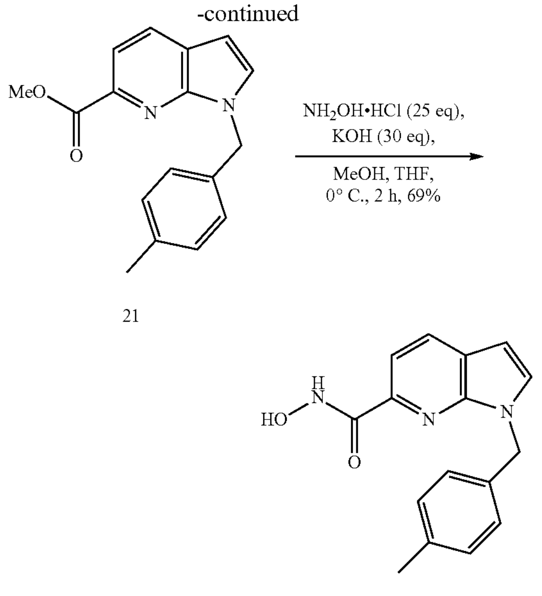

21

22

Synthesis of methyl 1-(4-methylbenzyl)-1H-pyrrolo[2,3-b]pyridine-6-carboxylate (21): SJ-3-112 To a solution of methyl 1H-pyrrolo[2,3-b]pyridine-6-carboxylate (5, 75 mg, 0.42 mmol) in DMF (5.0 mL) was added $Cs_2CO_3$ (150 mg, 0.46 mmol), followed by 1-(bromomethyl)-4-methylbenzene (20, 77.7 mg, 0.42 mmol). The resulting mixture was stirred at room temperature for 16 hours. Water and ethyl acetate were added to the reaction mixture. The reaction mixture was partitioned in ethyl acetate and water. Ethyl acetate layer was separated, and aqueous layer was extracted with ethyl acetate (2×20 mL) and the combined organic layer was washed with water, brine, and dried over sodium sulfate to yield a clear, free-flowing liquid. The residue was purified by column chromatography (Isco) using 5-20% hexanes-ethyl acetate to get methyl 1-(4-methylbenzyl)-1H-pyrrolo[2,3-b]pyridine-6-carboxylate (21, 99.0 mg, 84%) as colorless liquid. $^{1}H$ NMR (600 Hz, $CDCl_3$) δ 7.98 (q, J=8.3 Hz, 2H), 7.30 (d, J=3.3 Hz, 1H), 7.15 (d, J=8.1 Hz, 2H), 7.11 (d, J=8.2 Hz, 2H), 6.51 (d, J=3.7 Hz, 1H), 5.53 (s, 2H), 4.01 (s, 3H), 2.31 (s, 3H); $^{13}C$ NMR (150 Hz, $CDCl_3$) 166.8, 147.2, 140.8, 137.5, 134.2, 131.3, 129.4, 128.6, 128.0, 123.4, 117.4, 100.3, 52.6, 47.7, 21.1 ppm.

Synthesis of N-hydroxy-1-(4-methylbenzyl)-1H-pyrrolo[2,3-b]pyridine-6-carboxamide (22): To an ice-cooled solution of hydroxylamine hydrochloride (563 mg, 8.03 mmol) in methanol (10 mL) was added powdered KOH (538 mg, 9.60 mmol) portion wise and the resulting mixture was stirred at room temperature for 1 hour after the addition of KOH was completed. The precipitate was filtered off and the filtrate was added dropwise to an ice-cooled solution methyl 1-(4-methylbenzyl)-1H-pyrrolo[2,3-b]pyridine-6-carboxylate (21, 98.0 mg, 0.35 mmol) in methanol (5.0 mL). An additional amount of KOH (180 mg, 3.50 mmol) was added to the reaction solution and the reaction was monitored by TLC using MeOH: $CH_2Cl_2$ (1:9) solvent system at 0° C. After reaction completion (1 h), the pH of the solution was adjusted to pH 7.0-8.0 by dropwise addition of 1 M HCl, and solid product was filtered off and washed with water and hexanes and dried under vacuum to yield N-hydroxy-1-(4-methylbenzyl)-1H-pyrrolo[2,3-b]pyridine-6-carboxamide (22) as a gray color solid (68.0 mg, 69%). $^{1}H$ NMR (600 Hz, DMSO$_{d6}$) δ 11.45 (s, 1H), 9.07 (s, 1H), 8.09 (d, J=8.0 Hz, 1H), 7.74-7.70 (m, 2H), 7.28 (d, J=8.2 Hz, 2H), 7.10 (d, J=8.0 Hz, 2H), 6.56 (d, J=3.6 Hz, 1H), 5.56 (s, 2H), 2.24 (s, 3H); $^{13}$C NMR (150 Hz, DMSO$_{d6}$): 162.2, 145.4, 142.6, 136.5, 135.4, 131.5, 129.0, 128.9, 127.9, 127.8, 121.9, 113.5, 100.6, 46.5, 20.6 ppm; HRMS (ESI) m/z [M-H]$^+$ calcd for $C_{16}H_{14}O_2N_3$ 280.11081; found 280.1082.

The compounds were evaluated in the HDAC selectivity assays. This quantitative assay was used for iterative rounds of design synthesis and testing.

Cellular thermal shift assay (CETSA) was developed from the same principles of ligand induced thermal stability assays (TSA) of proteins. During TSA, purified proteins are heated in the absence or presence of ligand and then quickly cooled. Proteins that are bound to ligand are more thermally stable than their unbound counterparts, and these "thermal shifts" can be detected by various methods. CETSA uses cell lysates heated to different temperatures and quantifies the target protein in the soluble fraction by western blot. CETSA is a direct measurement of $IC_{50}$ through the measurement of the biophysical properties that stabilized the protein-ligand complex under thermal denaturation. The UPHH-00171 compound was tested in the CETSA assay, specifically for $HDAC_8$ binding. FIG. 1 shows CETSA demonstrating increase in thermal stability of $HDAC_8$ in the presence of UPHH-00171 compared to a control with no compound.

The gentamicin-induced AKI in zebrafish larvae (zfAKI assay), recapitulates injury and proliferation-based repair in mammalian AKI, but allows for higher throughput analysis of compound efficacy in AKI than mouse models. As fish are soaked in compounds, this assay is not subject to drug delivery and absorption problems that occur in early drug discovery in mice. This assay was used as a primary screening assay with the throughput being increased. UPHH-00171 was tested at two different doses in the zfAKI assay and both doses were found to increase survival as compared to the untreated control.

Figure 2:
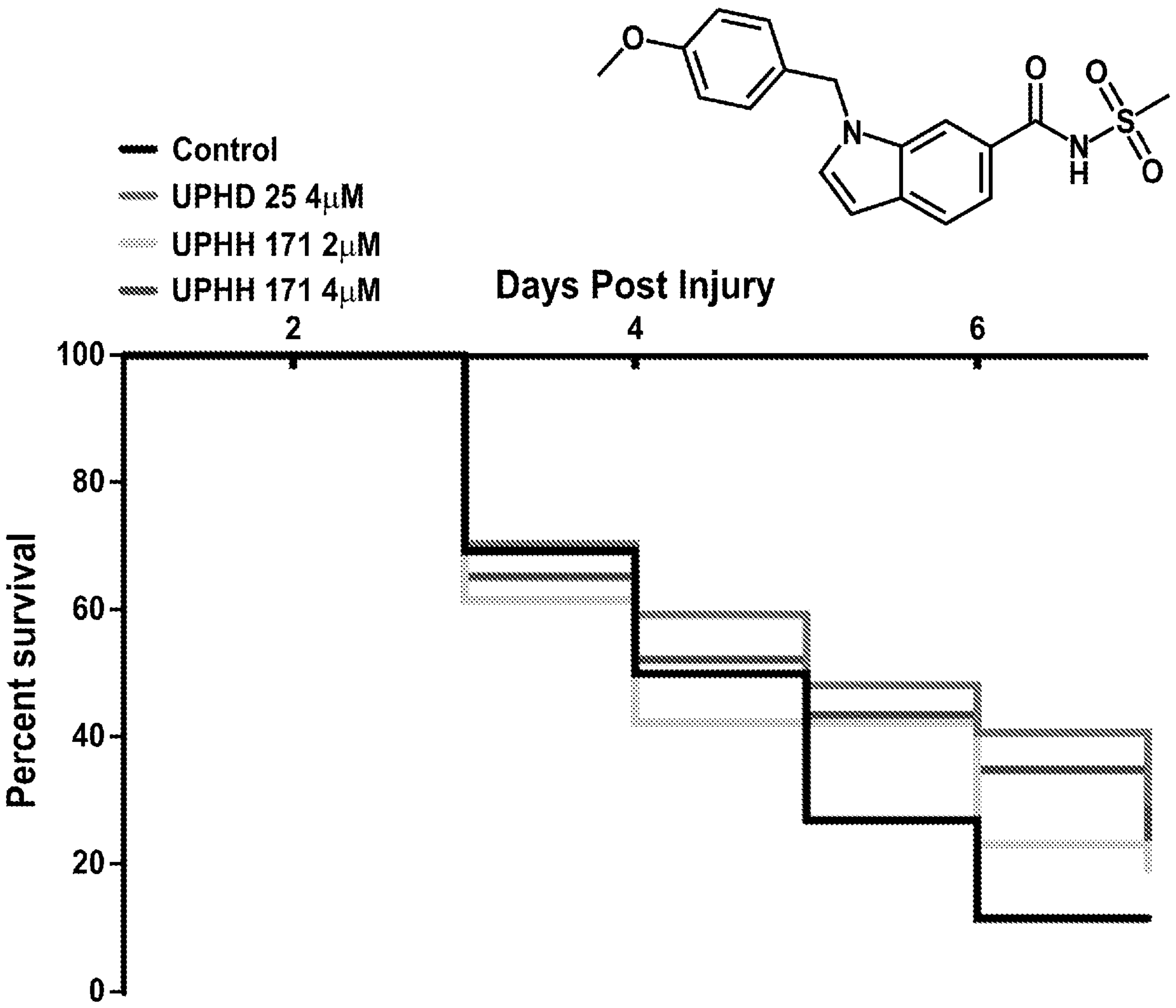
FIG. 2 is a graph showing Kaplan-Meier survival assay for UPHH-00171 compared to UPHD 25 treated and non-compound treated controls in AKI fish.

FIG. 2 shows the Kaplan-Meier survival assays for UPHH-00171 compared to UPHD 25 treated control and non-compound treated AKI fish.

Example 2: Blood Pharmacokinetics of UPHH-123 Following a Single Intraperitoneal (Dose: 10.4 mg/kg and 52 mg/kg) Administration in Male CD1 Mice

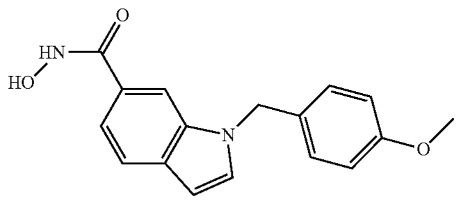 [SMILES: COc1ccc(Cn2ccc3ccc(C(=O)NO)cc32)cc1]

UPHH-00123 (PCI-34051)

The objective of this example was to investigate the blood pharmacokinetics of UPHH-123 in male CD1 mice following a single intraperitoneal dose administration. Eighteen male CD1 mice were divided in two groups as, Group 1 and Group 2 comprising nine mice in each group.

Animals in Group 1 were administered intraperitoneally with UPHH-123 solution formulation in 5% NMP, 5% Solutol HS, 30% PEG-400 and 60% normal saline at 10.4 mg/kg dose. Animals in Group 2 were administered intraperitoneally with UPHH-123 solution formulation in 5% NMP, 5% Solutol HS, 30% PEG-400 and 60% normal saline) at 52 mg/kg dose.

Blood samples (approximately 120 µL) were collected at pre-dose, 0.08, 0.25, 0.5, 1, 2, 4, 8 and 24 hr. The blood samples were collected at each time point in a labeled micro centrifuge tube containing K2EDTA as anticoagulant. Immediately aliquot (50 µL) of blood was hemolyzed with equal volume of water (50 µL) and quenched with three volume (150 µL) of acetonitrile (IS containing acetonitrile) and samples were stored below −70° C. until bioanalysis. All samples were processed for analysis by protein precipitation using acetonitrile (ACN) and analyzed with fit for purpose LC/MS/MS method (LLOQ: 10.04 ng/mL for UPHH-123 in blood). Pharmacokinetic parameters were calculated using the non-compartmental analysis tool of Phoenix WinNonlin (Version 7.0). Mean pharmacokinetic parameters are summarized below:

TABLE 1

Mean blood pharmacokinetic parameters of UPHH-123 following a single intraperitoneal dose administration to male CD1 mice (Dose: 10.4 and 52 mg/kg)

| Compound | Route | Matrix | Dose (mg/kg) | $T_{max}$ (hr) | $C_{max}$ (ng/mL) | $AUC_{last}$ (hr*ng/mL) | $AUC_{inf}$ (hr*ng/mL) |
|---|---|---|---|---|---|---|---|
| UPHH-123 | IP | Blood | 10.4 | 0.25 | 3808.35 | 1851.75 | 1954.64 |
| | | | 52 | 0.08 | 6157.82 | 6680.90 | 7636.25 |

UPHH-123:

Group I—10.4 mg/kg: Following a single intraperitoneal administration of UPHH-123 to male CD1 mice at 10.4 mg/kg dose, blood concentrations were quantifiable up to 24 hr (1 animal out of 3) with mean $T_{max}$ at 0.25 hr.

Group II—52 mg/kg: Following a single intraperitoneal administration of UPHH-123 to male CD1 mice at 52 mg/kg dose, blood concentrations were quantifiable up to 24 hr (1 animal out of 3) with mean $T_{max}$ at 0.08 hr.

In general, dose related increase (3.6-fold) in plasma exposure was observed from 10.4 to 52 mg/kg dose.

TABLE 2

Individual blood concentration-time data of UPHH-123 following a single intraperitoneal administration to male CD1 mice (Group 1; Dose: 10.4 mg/kg)

| | Blood Concentration (ng/mL) Time (hr) | | | | | | | | |
|---|---|---|---|---|---|---|---|---|---|
| Animal ID | Pre-dose | 0.08 | 0.25 | 0.5 | 1 | 2 | 4 | 8 | 24 |
| 1 | 0.00 | | | 848.67 | | | 92.93 | | |
| 2 | 0.00 | | | 518.79 | | | 47.81 | | |
| 3 | 0.00 | | | 675.87 | | | 118.38 | | |
| 4 | | 1604.08 | | | 158.26 | | | 23.94 | |
| 5 | | 2082.46 | | | 105.72 | | | 26.21 | |
| 6 | | 2293.56 | | | 180.27 | | | 17.80 | |
| 7 | | | 4437.91 | | | 39.90 | | | 0.00 |
| 8 | | | 2572.69 | | | 98.73 | | | 0.00 |
| 9 | | | 4414.44 | | | 125.25 | | | 14.58 |
| Mean | 0.00 | 1993.37 | 3808.35 | 681.11 | 148.08 | 87.96 | 86.37 | 22.65 | 14.58[c] |
| SD | 0.00 | 353.27 | 1070.17 | 165.00 | 38.30 | 43.68 | 35.74 | 4.35 | NA |
| % CV | NA | 17.72 | 28.10 | 24.23 | 25.87 | 49.66 | 41.38 | 19.21 | NA |

LLOQ = 10.04 ng/mL;

NA—not applicable;

[c]Value excluded from data analysis

No peak or values below LLOQ were considered as zero for data analysis

TABLE 3

Individual blood concentration-time data of UPHH-123 following a single intraperitoneal administration to male CD1 mice (Group 2; Dose: 52 mg/kg)

| | Blood Concentration (ng/mL) Time (hr) | | | | | | | | |
|---|---|---|---|---|---|---|---|---|---|
| Animal ID | Pre-dose | 0.08 | 0.25 | 0.5 | 1 | 2 | 4 | 8 | 24 |
| 10 | 0.00 | | | 4708.54 | | | 125.55 | | |
| 11 | 0.00 | | | 3225.37 | | | 442.67 | | |
| 12 | 0.00 | | | 3520.30 | | | 145.43 | | |
| 13 | | 5996.22 | | | 2284.83 | | | 160.02 | |
| 14 | | 7841.88 | | | 2031.75 | | | 167.15 | |
| 15 | | 4635.35 | | | 2659.04 | | | 107.02 | |
| 16 | | | 5280.55 | | | 315.76 | | | 0.00 |
| 17 | | | 6058.02 | | | 238.47 | | | 0.00 |
| 18 | | | 5694.33 | | | 525.92 | | | 10.38 |
| Mean | 0.00 | 6157.82 | 5677.63 | 3818.07 | 2325.21 | 360.05 | 237.88 | 144.73 | 10.38[c] |
| SD | 0.00 | 1609.36 | 389.00 | 785.14 | 315.59 | 148.76 | 177.63 | 32.85 | NA |
| % CV | NA | 26.14 | 6.85 | 20.56 | 13.57 | 41.32 | 74.67 | 22.70 | NA |

LLOQ = 10.04 ng/mL;

NA—not applicable;

[c]Value excluded from data analysts

No peak or values below LLOQ were considered as zero far data analysis

Figure 3:
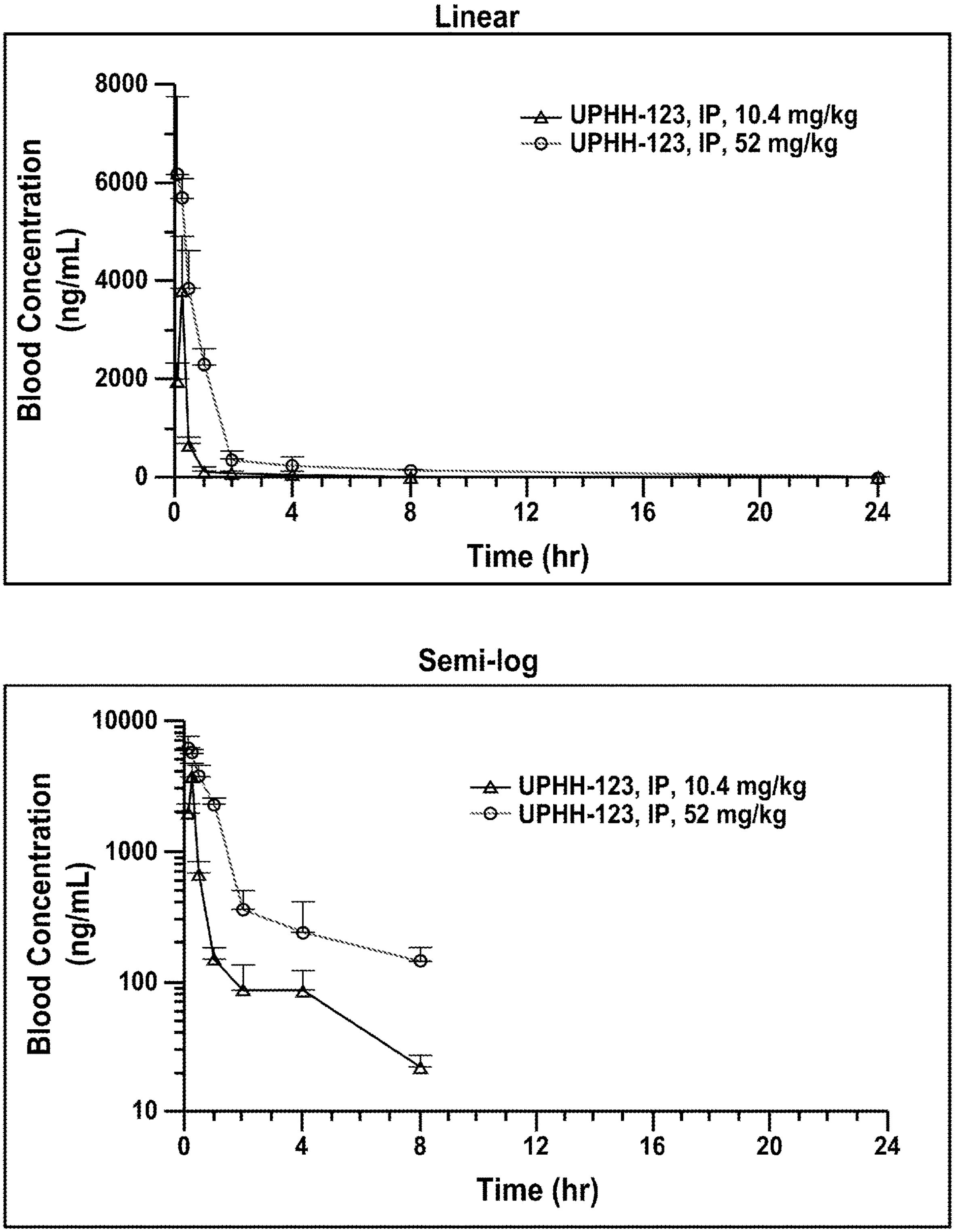
FIG. 3 include two graphs showing the mean blood concentration-time profile of UPHH-123 (PCI-34051) following a single intraperitoneal dose administration to male CD1 mice (Dose: 10.4 mg/kg (top graph) and 52 mg/kg (bottom graph)).

FIG. 3 shows the mean blood concentration-time profile of UPHH-123 following a single intraperitoneal dose administration to male CD1 mice (Dose: 10.4 and 52 mg/kg)

Example 4: Plasma Pharmacokinetics of UPHH-000171 Following a Single Intraperitoneal Dose Administration to Male CD1 Mice at 10 and 50 mg/kg Dose

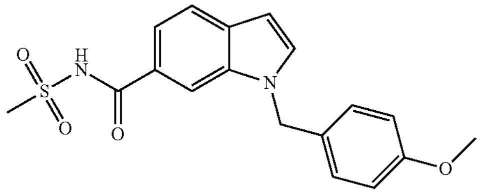

1-(4-methoxybenzyl)-N-(methylsulfonyl)-1H-indole-6-carboxamide (UPHH-00171)

The objective of this example was to investigate the plasma pharmacokinetics of UPHH-000171 following a single intraperitoneal dose administration to male CD1 mice at 10 and 50 mg/kg. Eighteen male mice were divided in to two groups with nine animals in each group, Group 1: UPHH-000171; 10 mg/kg/IP; Animal #1-9

Group 2: UPHH-000171; 50 mg/kg/IP; Animal #10-18.

Animals in Group 1 and Group 2 were administered with solution formulation of UPHH-000171 in 5% NMP, 25% Solutol HS-15 and 70% normal saline intraperitoneally at 10 and 50 mg/kg dose, respectively.

The blood samples were collected from set of three mice at each time point in labeled micro centrifuge tube containing K2EDTA solution as anticoagulant at Pre-dose, 0.08, 0.25, 0.5, 1, 2, 4, 8 and 24 hr. Plasma samples were separated by centrifugation of whole blood and stored below −70±10° C. until bioanalysis. All samples were processed for analysis by protein precipitation using acetonitrile and analyzed with fit-for-purpose LC-MS/MS method (LLOQ=10.38 ng/mL). Pharmacokinetic parameters were calculated using the non-compartmental analysis tool of Phoenix WinNonlin® (Version 7.0). Mean pharmacokinetic parameters are summarized below:

TABLE 4

Plasma pharmacokinetic parameters of UPHH-000171 following a single intraperitoneal dose administration to male CD1 mice (Dose: 10 and 50 mg/kg)

| Compound | Route | Dose (mg/kg) | $T_{max}$ (hr) | $C_{max}$ (ng/mL) | $AUC_{last}$ (hr*ng/mL) | $AUC_{inf}$ (hr*ng/mL) |
|---|---|---|---|---|---|---|
| UPHH-000171 | IP | 10 | 4.00 | 50942.03 | 557738.48 | NC |
| (KL-2-167) | | 50 | 1.00 | 228068.10 | 1763281.74 | 1767417.41 |

NC - Not calculated due to insufficient data.

10 mg/kg/IP: Following a single intraperitoneal dose administration of UPHH-000171 at 10 mg/kg to male CD1 mice, plasma concentrations were quantifiable up to 24 hr with $T_{max}$ of 4 hr.

50 mg/kg/IP: Following a single intraperitoneal dose administration of UPHH-000171 at 50 mg/kg to male CD1 mice, plasma concentrations were quantifiable up to 24 hr with $T_{max}$ of 1 hr.

In general, dose related increase (3-fold) in plasma exposure ($AUC_{last}$) was observed from 10 mg/kg to 50 mg/kg dose.

TABLE 5

Individual plasma concentration-time data of UPHH-000171 following a single intraperitoneal administration to male CD1 mice (Dose: 10 mg/kg)

| | Plasma Concentration (ng/mL) Time (hr) | | | | | | | | |
|---|---|---|---|---|---|---|---|---|---|
| Animal ID | Pre-dose | 0.08 | 0.25 | 0.5 | 1 | 2 | 4 | 8 | 24 |
| 1 | 0.00 | | | 36468.73 | | | 31815.34 | | |
| 2 | 0.00 | | | 45578.93 | | | 47512.89 | | |
| 3 | 0.00 | | | 41628.22 | | | 73497.85 | | |
| 4 | | 9871.25 | | | 49594.52 | | | 35142.30 | |
| 5 | | 2877.79 | | | 19264.72 | | | 20138.85 | |
| 6 | | 7508.44 | | | 34912.30 | | | 29805.54 | |
| 7 | | | 32979.11 | | | 53558.23 | | | 2930.59[e] |
| 8 | | | 28861.97 | | | 46853.15 | | | 131.01 |
| 9 | | | 28672.95 | | | 43408.40 | | | 68.44 |

TABLE 5-continued

Individual plasma concentration-time data of UPHH-000171 following a single intraperitoneal administration to male CD1 mice (Dose: 10 mg/kg)

| Animal ID | Pre-dose | Plasma Concentration (ng/mL) Time (hr) 0.08 | 0.25 | 0.5 | 1 | 2 | 4 | 8 | 24 |
|---|---|---|---|---|---|---|---|---|---|
| Mean | 0.00 | 6752.49 | 30171.34 | 41225.29 | 34590.51 | 47939.93 | 50942.03 | 28362.23 | 99.73[d] |
| SD | 0.00 | 3557.49 | 2433.43 | 4568.45 | 15167.46 | 5161.45 | 21051.77 | 7605.15 | NA |
| CV % | NA | 52.7 | 8.1 | 11.1 | 43.8 | 10.8 | 41.3 | 26.8 | NA |

LLOQ = 10.38 ng/mL;
NA—not applicable;
No peaks or values below LLOQ were considered as zero for data analysis;
[d]Average of two values reported and considered for data analysis and graphical representation;
[e]Value excluded from data analysis as an outlier.

TABLE 6

Individual plasma concentration-time data of UPHH-000171 following a single intraperitoneal administration to male CD1 mice (Dose: 50 mg/kg)

| Animal ID | Pre-dose | Plasma Concentration (ng/mL) Time (hr) 0.08 | 0.25 | 0.5 | 1 | 2 | 4 | 8 | 24 |
|---|---|---|---|---|---|---|---|---|---|
| 10 | 0.00 | | | 47522.98 | | | 115510.21 | | |
| 11 | 0.00 | | | 137922.52 | | | 127613.87 | | |
| 12 | 0.00 | | | 96505.03 | | | 106201.99 | | |
| 13 | | 88980.96 | | | 229384.71 | | | 102026.16 | |
| 14 | | 59305.08 | | | 218799.23 | | | 93195.14 | |
| 15 | | 90638.28 | | | 236020.35 | | | 75070.05 | |
| 16 | | | 31701.46 | | | 93162.33 | | | 1407.79 |
| 17 | | | 171000.65 | | | 195094.83 | | | 391.49 |
| 18 | | | 182938.71 | | | 235858.27 | | | 1081.42 |
| Mean | 0.00 | 79641.44 | 128546.94 | 93983.51 | 228068.10 | 174705.14 | 116442.02 | 90097.12 | 960.23 |
| SD | 0.00 | 17631.29 | 84082.78 | 45252.49 | 8685.73 | 73500.59 | 10736.31 | 13742.50 | 518.87 |
| CV % | NA | 22.1 | 65.4 | 48.1 | 3.8 | 42.1 | 9.2 | 15.3 | 54.0 |

LLOQ = 10.38 ng/mL;
NA—not applicable;
No peaks or values below LLOQ were considered as zero for data analysis.

Figure 4:
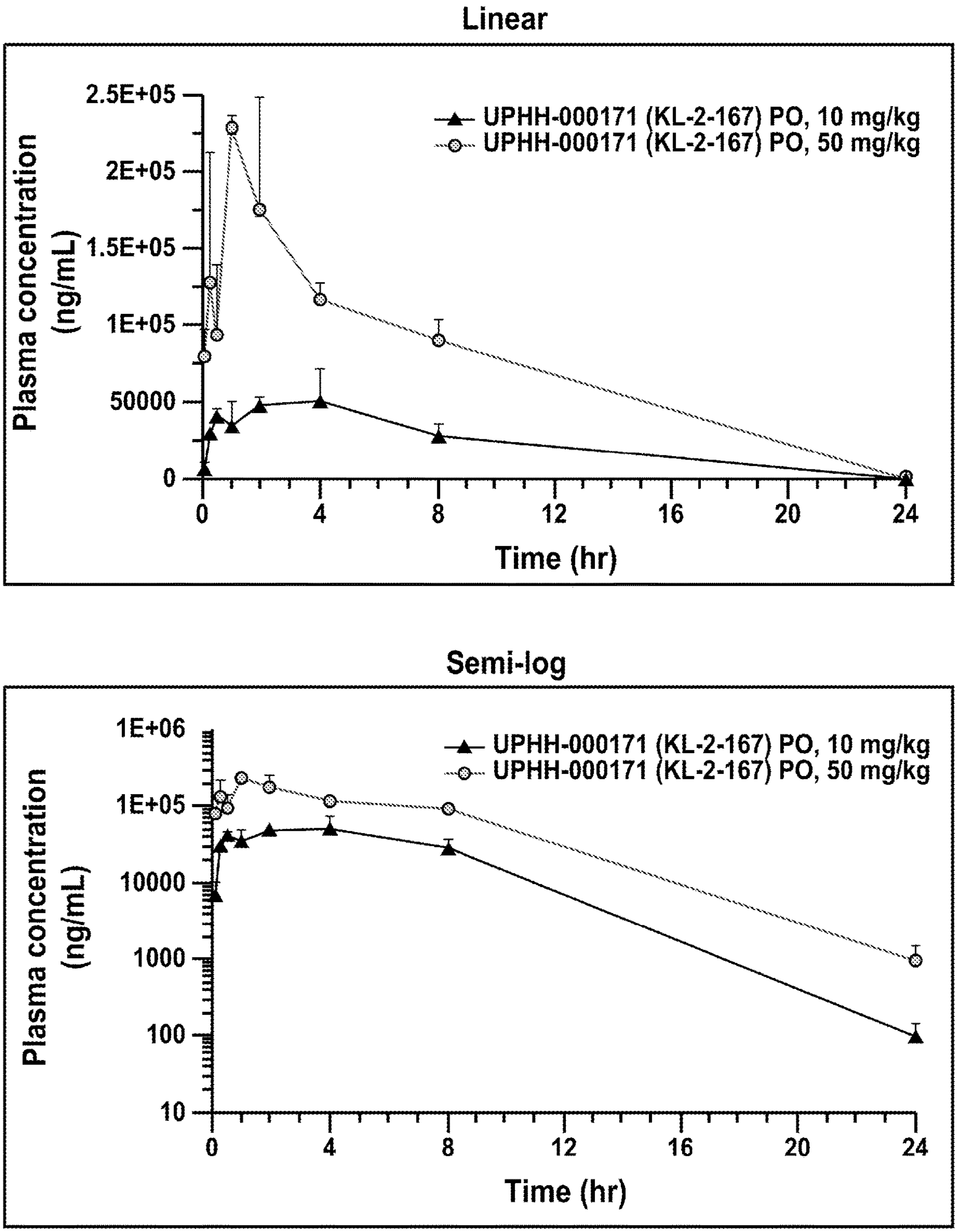
FIG. 4 include two graphs showing the mean plasma concentration-time profile of UPHH-000171 following a single intraperitoneal dose administration in male CD1 mice (Dose: 10 mg/kg (top graph) and 50 mg/kg (bottom graph)).

FIG. 4 shows the mean plasma concentration-time profile of UPHH-000171 following a single intraperitoneal dose administration in male CD1 mice (Dose: 10 and 50 mg/kg).

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. A compound having a structure according to Formula I-A-9:

Formula I-A-9

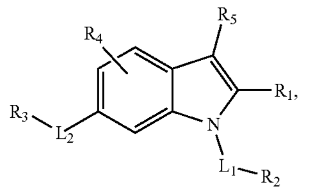

wherein $L_1$ is a linker selected from a bond, —$C_1$-$C_6$ alkylene-, —$C_1$-$C_6$ alkoxy-, and —$C_1$-$C_6$ alkylamide-, and wherein $L_1$ is optionally substituted with one or more groups;

$L_2$ is a linker selected from a bond, and —$C_1$-$C_6$ alkylene-, and wherein $L_2$ is optionally substituted with one or more groups;

$R_1$ is selected from hydrogen, and $C_1$-$C_6$ alkyl, wherein $R_1$ is optionally substituted or unsubstituted;

$R_2$ is selected from aryl, and heteroaryl, wherein $R_2$ is substituted with one or more groups selected from alkyl, haloalkyl, alkoxy, haloalkoxy, amine, alkylamine, amide, alkylamide, hydroxyl, cycloalkyl, heterocycloalkyl, cyano, nitro, ester, and —$SF_5$;

$R_3$ is selected from wherein R'', and R''' are independently selected from hydrogen, $C_1$-$C_6$ alkyl, $C_1$-$C_6$ haloalkyl, substituted or unsubstituted cycloalkyl, or unsubstituted cycloalkenyl, substituted or unsubstituted heterocycloalkenyl, heterocycloalkyl, cycloheteroalkenyl, substituted or unsubstituted aryl, or substituted or unsubstituted heteroaryl;

$R_4$ is selected from hydrogen, halogen, alkyl, haloalkyl, and heteroalkyl, and wherein $R_4$ is optionally substituted with one or more groups; and $R_5$ is selected from hydrogen, and $C_1$-$C_6$ alkyl;

or a pharmaceutically acceptable salt, ester, or prodrug thereof.

2. The compound of claim 1, wherein $L_1$ is —$C_1$-$C_3$ alkylene, —$C_1$-$C_3$ alkoxy-, or —$C_1$-$C_3$ alkylamide-.

3. The compound of claim 1, wherein $L_2$ is a bond.

4. The compound of claim 1, wherein $R_1$, $R_4$, and $R_5$ are hydrogen.

5. The compound of claim 1, wherein $R_1$ and $R_5$ are hydrogen.

6. The compound of claim 1, wherein $R_2$ is aryl, wherein $R_2$ is substituted with one or more groups selected from alkyl, haloalkyl, alkoxy, haloalkoxy, amine, alkylamine, amide, alkylamide, alkyl heterocycloalkyl, hydroxyl, cyano, nitro, ester, $SF_5$, or haloalkyl.

7. The compound of claim 1, wherein $R_2$ is selected from phenyl, benzodioxole, or pyridinyl, wherein $R_2$ is substituted with one or more alkoxy groups, alkyl heterocycloalkyl, or a combination thereof.

8. The compound of claim 1, wherein $R_3$ is —$CONHSO_2R''$, wherein R'' is selected from hydrogen, $C_1$-$C_6$ alkyl, and $C_1$-$C_6$ haloalkyl.

9. The compound of claim 1, wherein the compound has a structure below:

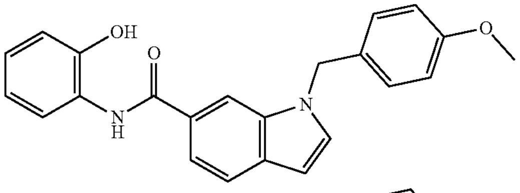

,

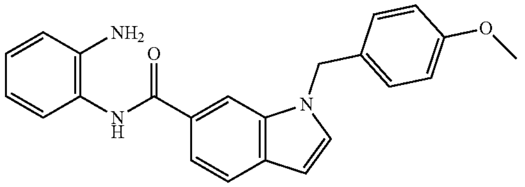

,

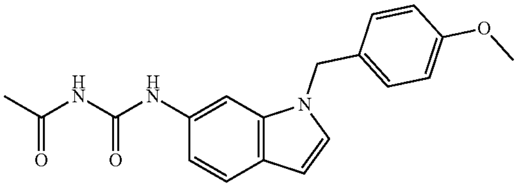

,

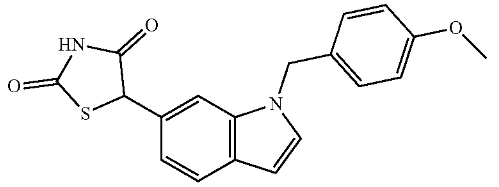

,

-continued

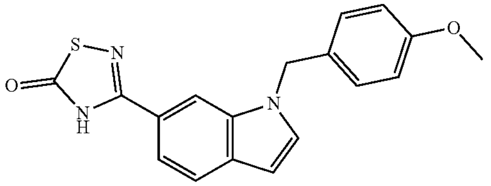

,

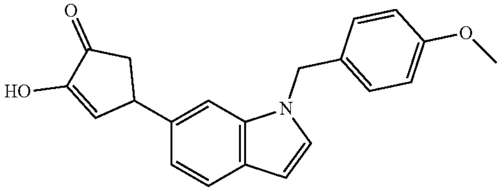

,

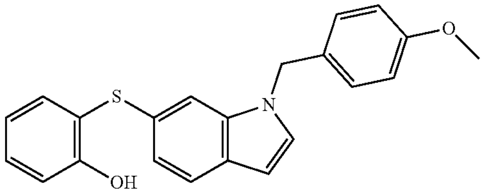

,

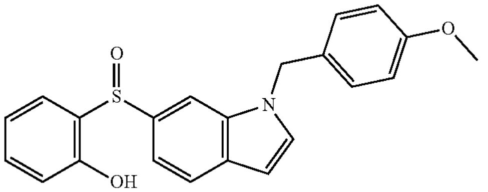

,

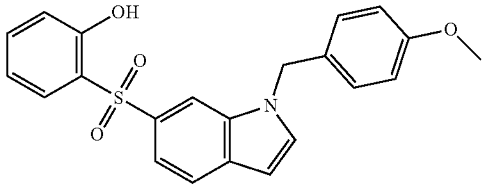

,

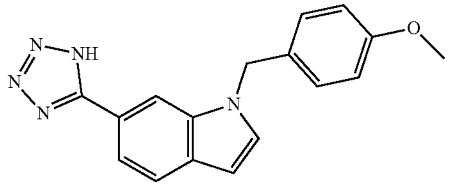

,

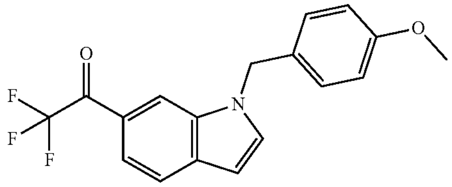

,

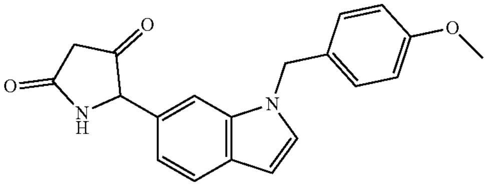

,

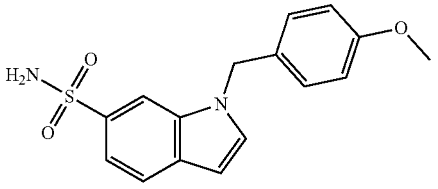

,

-continued
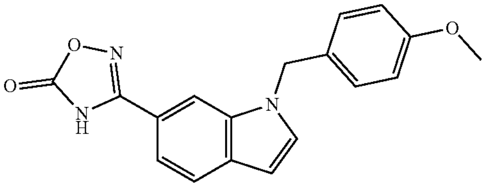
,
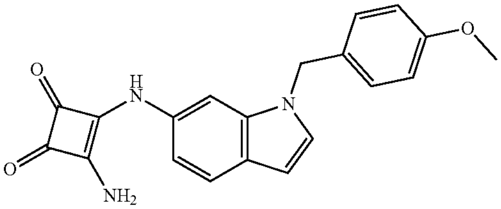
,
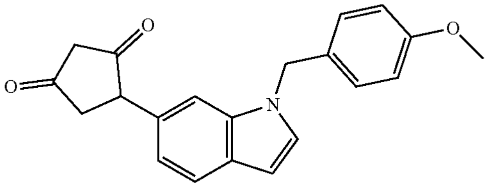
,
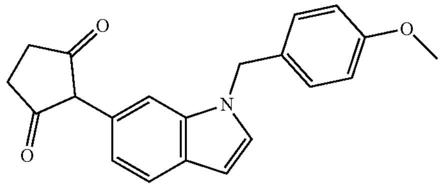
,
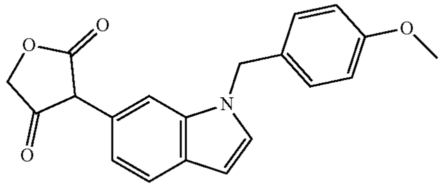
,
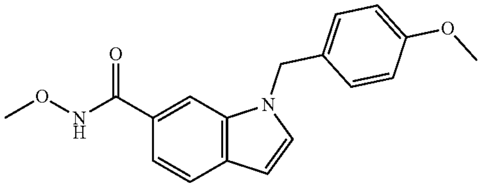
,
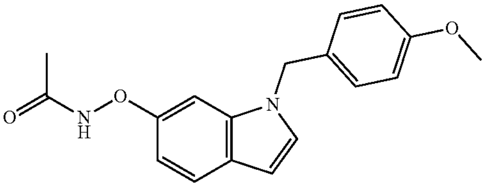
,
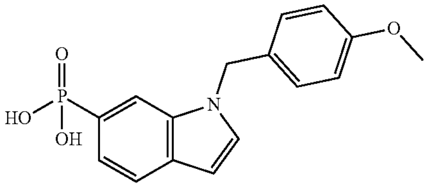
,
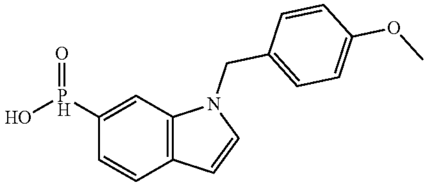
,
-continued
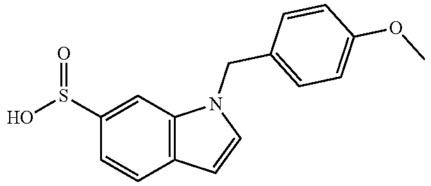
,
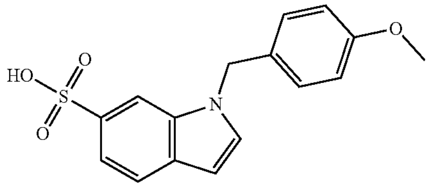
,
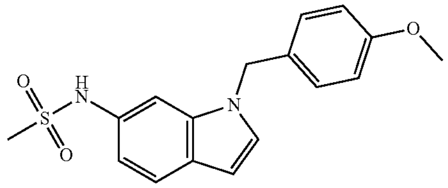
,
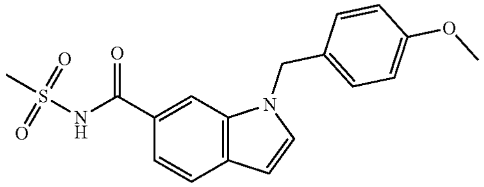
,
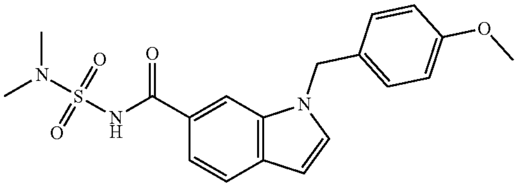
,
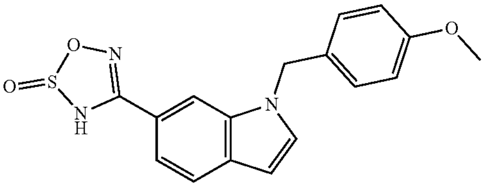
,
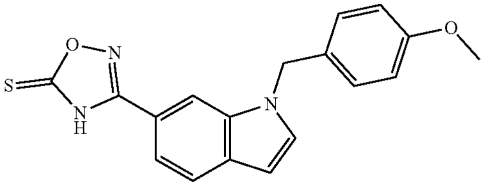
,
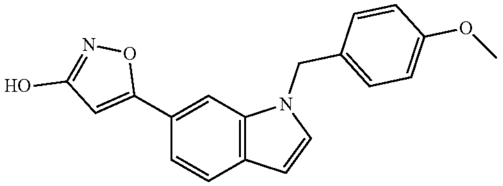
,
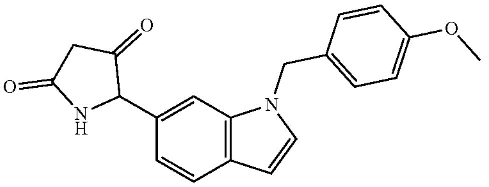
, -continued
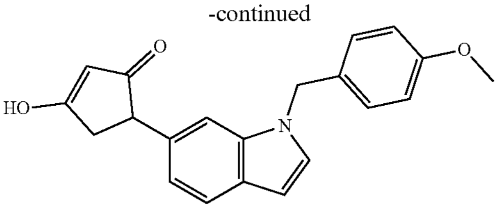
,
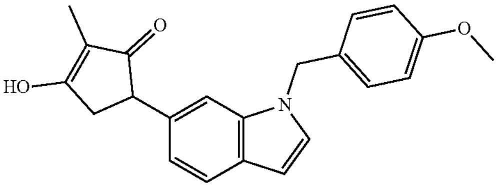
,
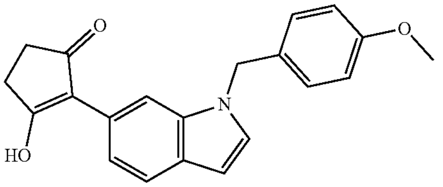
,
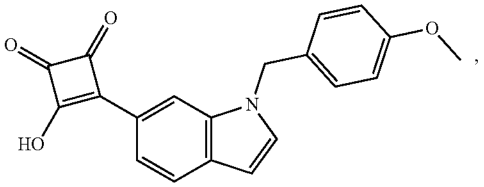
,
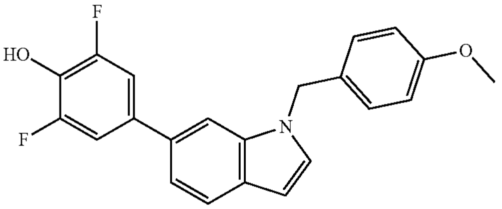
,
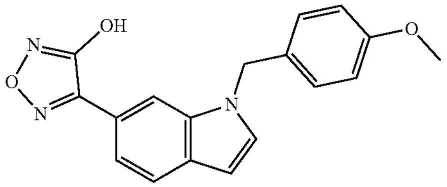
,
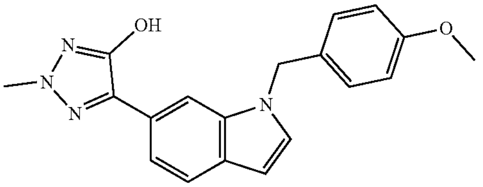
,
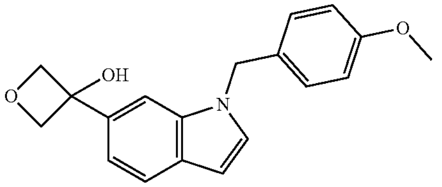
,
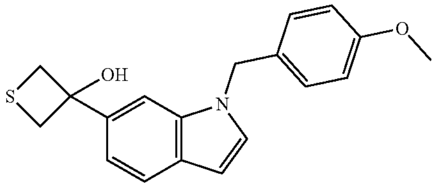
,
-continued
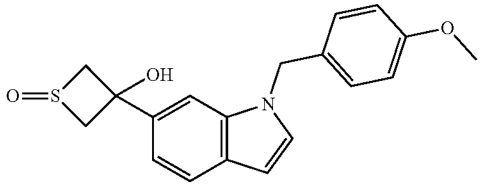
,
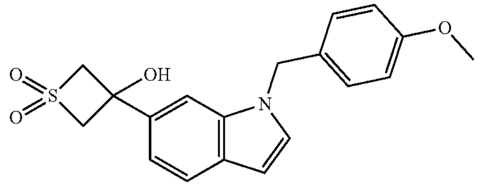
,
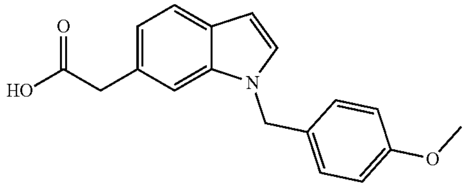
,
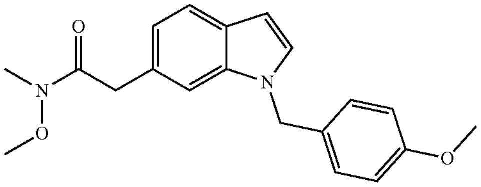
,
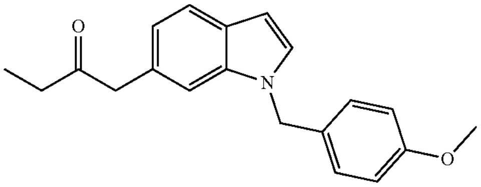
,
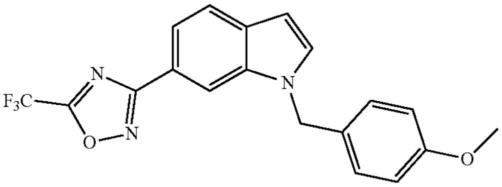
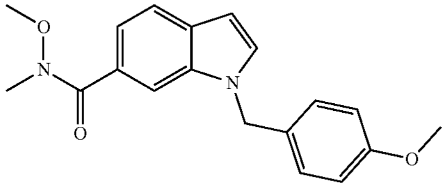
,
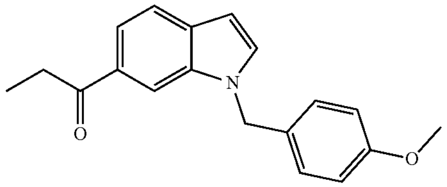
,
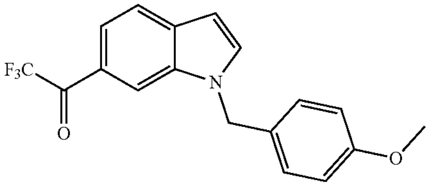
, -continued

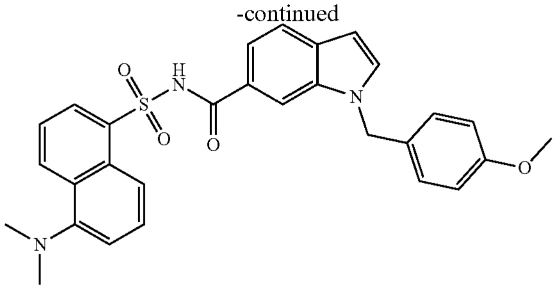

,

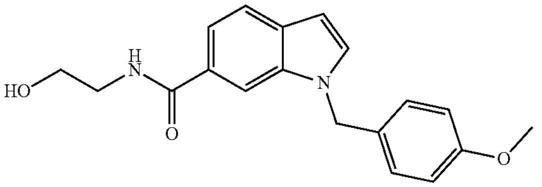

,

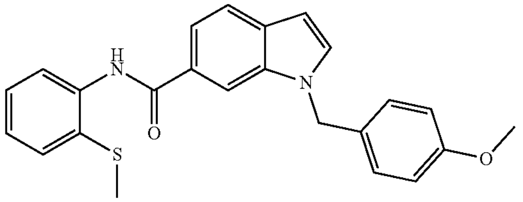

, or

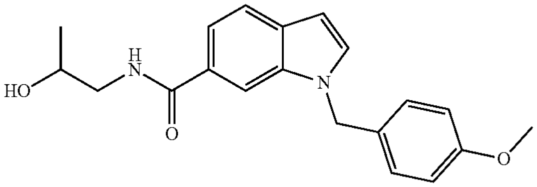

.

10. A pharmaceutical composition comprising a therapeutic effective amount of the compound of claim 1 and a pharmaceutically acceptable carrier.

11. A method of inhibiting histone deacetylases (HDACs) in a subject, the method comprising administering to the subject the pharmaceutical composition of claim 10.

12. The compound of claim 1, wherein $L_1$ is $—C_1\text{-}C_3$ alkylene.

13. The compound of claim 1, wherein $L_1$ is $—CH_2—$.

14. The compound of claim 1, wherein $R_3$ is $—C(O)NHSO_2CH_3$.

15. The compound of claim 1, wherein the compound has a structure of:

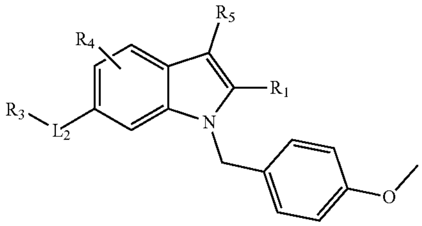

or a pharmaceutically acceptable salt, ester, or prodrug thereof.

16. The compound of claim 1, wherein the compound has a structure of:

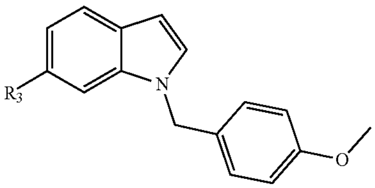

or a pharmaceutically acceptable salt, ester, or prodrug thereof.

17. The compound of claim 1, wherein the compound has a structure of:

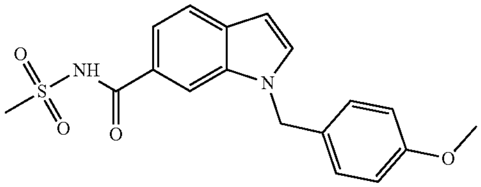

or a pharmaceutically acceptable salt, ester, or prodrug thereof.

* * * * *